(12) United States Patent (10) Patent No.: US 8,163,546 B2
Akamatsu et al. (45) Date of Patent: *Apr. 24, 2012

(54) MAMMALIAN CELL-BASED IMMUNOGLOBULIN DISPLAY LIBRARIES

(75) Inventors: Yoshiko Akamatsu, Fremont, CA (US); Tsuneaki Asai, Kanagawa (JP); Naoya Tsurushita, Palo Alto, CA (US)

(73) Assignee: Abbott Biotherapeutics Corp., Redwood City, CA (US)

( * ) Notice: Subject to any disclaimer, the term of this patent is extended or adjusted under 35 U.S.C. 154(b) by 58 days.

This patent is subject to a terminal disclaimer.

(21) Appl. No.: 12/748,247

(22) Filed: Mar. 26, 2010
(Under 37 CFR 1.47)

(65) Prior Publication Data

US 2011/0008883 A1 Jan. 13, 2011

Related U.S. Application Data

(63) Continuation of application No. 11/933,819, filed on Nov. 1, 2007, now Pat. No. 7,732,195.

(60) Provisional application No. 60/856,143, filed on Nov. 1, 2006.

(51) Int. Cl.
*C12N 15/00* (2006.01)
*C12N 5/00* (2006.01)
*G01N 33/567* (2006.01)

(52) U.S. Cl. ............ 435/320.1; 435/455; 435/325; 435/7.21

(58) Field of Classification Search ............ None
See application file for complete search history.

(56) References Cited

U.S. PATENT DOCUMENTS

| | | | |
|---|---|---|---|
| 4,816,567 A | 3/1989 | Cabilly et al. | |
| 5,264,357 A | 11/1993 | Caras et al. | |
| 7,732,195 B2 * | 6/2010 | Akamatsu et al. | 435/320.1 |
| 2005/0059082 A1 | 3/2005 | Breitling et al. | |
| 2005/0282181 A1 | 12/2005 | Yan et al. | |
| 2007/0111260 A1 | 5/2007 | Gao et al. | |

FOREIGN PATENT DOCUMENTS

| | | | |
|---|---|---|---|
| WO | WO 03/029456 A1 | 4/2003 | |
| WO | WO 2007/131774 A1 | 11/2007 | |

OTHER PUBLICATIONS

Brezinsky et al. "A simple method for enriching populations of transfected CHO cells for cells of higher specific productivity." J Immunol Methods. Jun. 1, 2003;277(1-2):141-55.
Browne et al. "Selection methods for high-producing mammalian cell lines." Trends Biotechnol. Sep. 2007;25(9):425-32.
Chestnut et al. "Selective isolation of transiently transfected cells from a mammalian cell population with vectors expressing a membrane anchored single-chain antibody." J Immunol Methods. Jun. 14, 1996;193(1):17-27.
International Search Report and the Written Opinion of the International Searching Authority for International Application No. PCT/US2007/083350, dated May 21, 2008.
International Search Report and the Written Opinion of the International Searching Authority for International Application No. PCT/US2008/082131, dated Sep. 29, 2009.
Li et al. "A comparative study of different vector designs for the mammalian expression of recombinant IgG antibodies." J Immunol Methods. Jan. 10, 2007;318(1-2):113-24.
Liao et al. "Design of transgenes for efficient expression of active chimeric proteins on mammalian cells." Biotechnol Bioeng. May 20, 2001;73(4):313-23.
Mattanovich et al. "Applications of cell sorting in biotechnology." Microb Cell Fact. Mar. 21, 2006;5:12.
Sharon et al. "Recombinant polyclonal antibody libraries." Comb Chem High Throughput Screen. Jun. 2000;3(3):185-96.

\* cited by examiner

*Primary Examiner* — Ilia Ouspenski

(57) ABSTRACT

Disclosed are mammalian cell surface display vectors for isolating and/or characterizing immunoglobulins and various uses thereof.

27 Claims, 9 Drawing Sheets

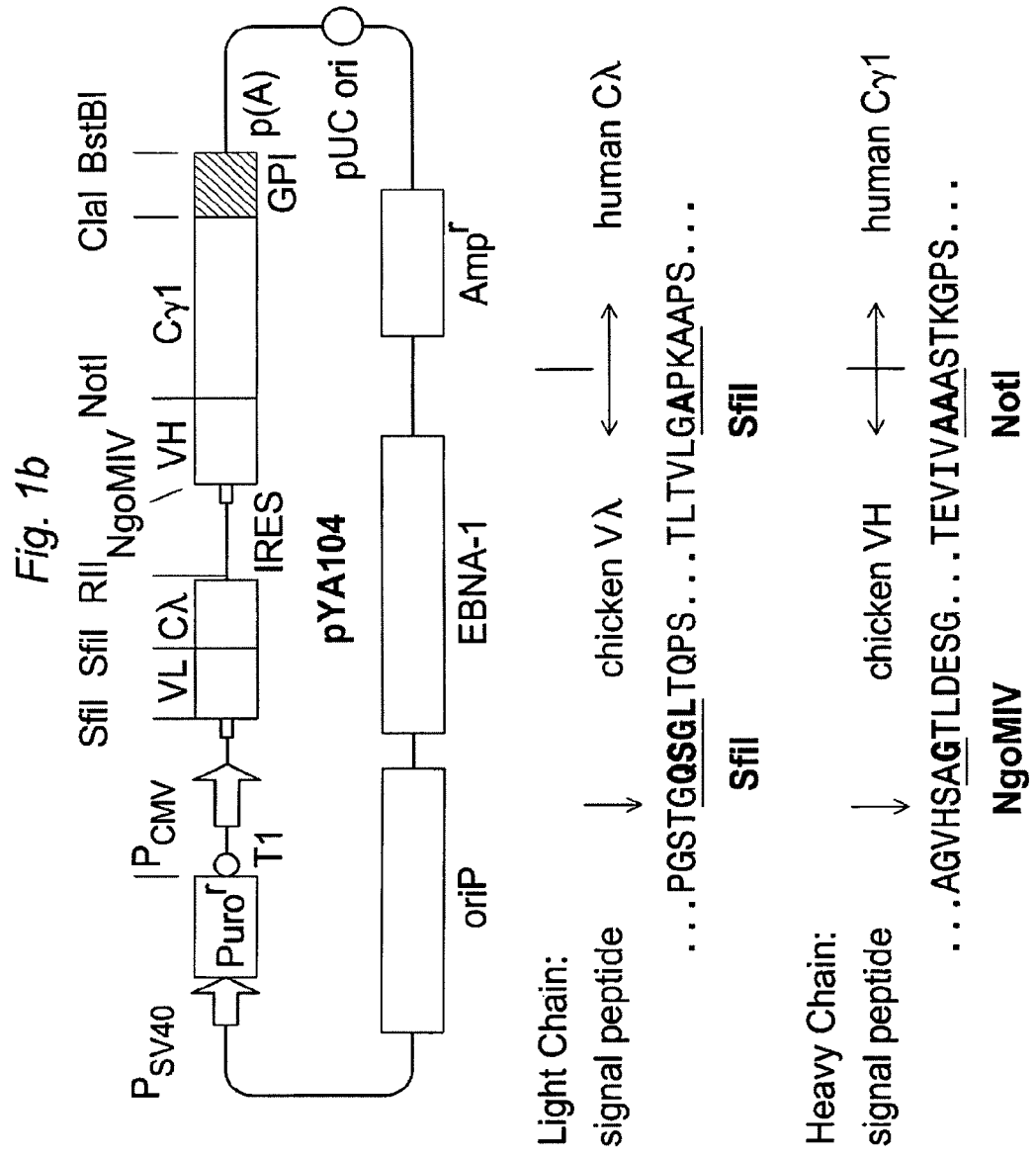

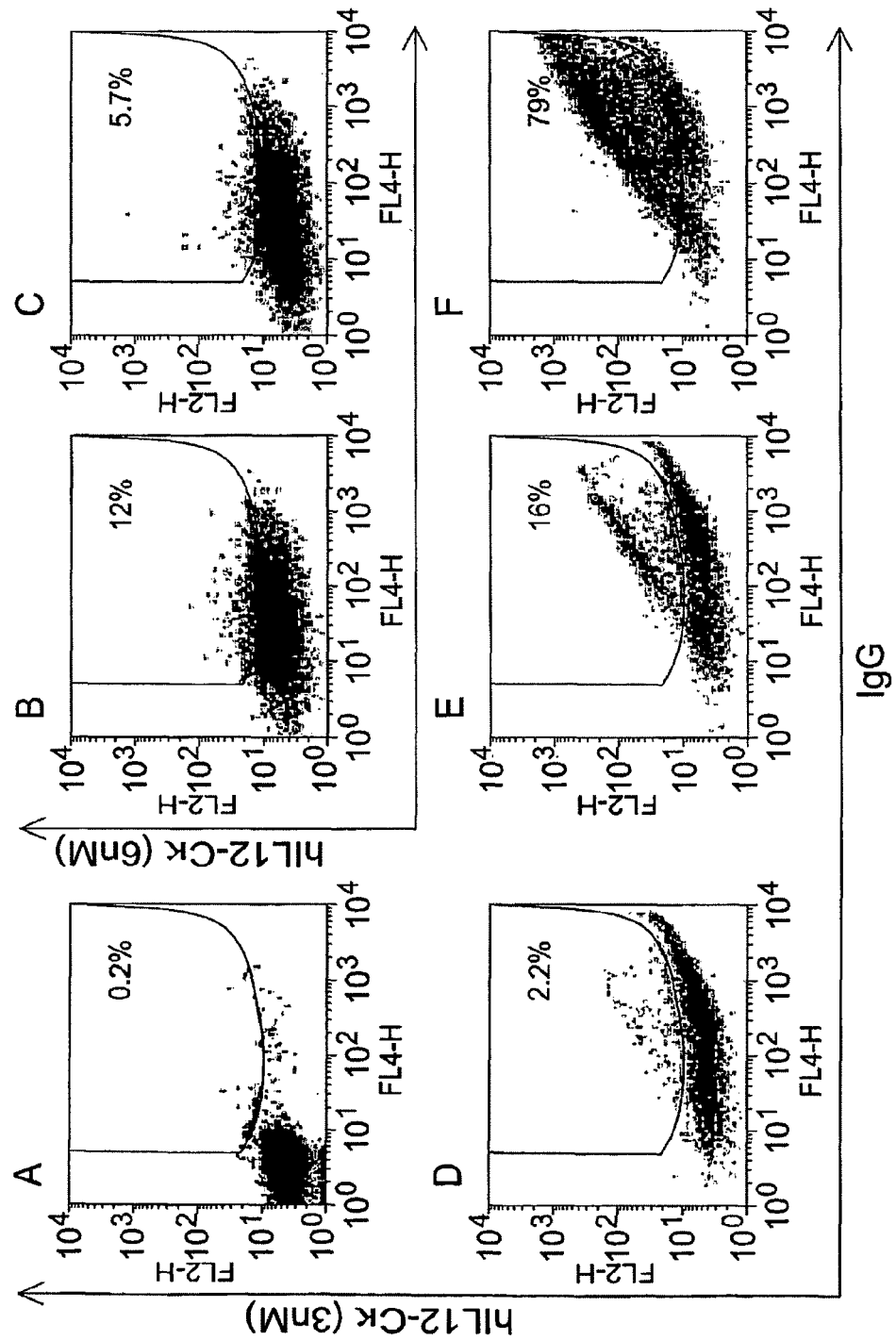

*Fig. 4a*

```
Vλ              1                   2                   3                   4
         123456789 0123456789 0123456789 0123456789 0123456789
                                                   A
Chicken GL  **ALTQPSS *VSANPGGTV KITCSGDS-- -SYYGWYQQKA PGSAPVTVIY
mh-C1       **GLTQPSS *VSANPGGTV EITCSGGG-- -GSYGWHQQKS PGSAPVTLIY
mh-E1       **VSANPGGTV KITCSGGG-- -GSYGWYQQKS PGSAPVTVIY
h-B1        **GLTQPSS *VSANPGGTV EITCSGSS-- -GSYGWYQQKS PGSAPVTVIY 5         6          7          8          9
         0123456789 0123456789 0123456789 0123456789 0123455555567ε
                                                            ABCDE
Chicken GL  DNTNRPSNIP SRFSGSKSGS TATLTITGVR ADDNAVYYCA STDSSSTA---GII
mh-C1       YNDKRPSNIP SRFSGSKSGS TSTLTITGVQ AEDEAVYFCG SYEGSTYAGYVGVI
mh-E1       ESTKRPSDIP SRFSGSASGS TATLTITGVQ VEDEAVYYCG GYDSSA---GII
h-B1        QNDKRPSDIP SRFSGSKSGS TATLTITGVR AEDEAVYYCG GYDRSNSS---GII 1
            0
         01234567
Chicken GL AGTTLTVL
mh-C1      AGTTLTVL
mh-E1      AGTTLTVL
h-B1       AGTTLTVL
```

```
                    1          2          3          4
          123456789 0123456789 0123456789 0123456789 0123456789
Chicken GL AVTLDESGG GLQTPGRALS LVCKASGFTF SSYNMGWVRQ APGKGLEFVA
mh-C1      AGTLDESGG GLQTPGGALS LVCKASGFTF SSHGMGWMRQ APGKGLEWVA
mh-E1      AGTLDESGG GLQTPGGALS LVCKASGFSF RSYDVAWVRQ APGKGLEWVA
h-B1       AGTLDESGG GLQTPGGALS LVCKASGFSF RSYDVAWVRQ APGKGLEWVA 5          6          7          8          9
           0122234567890123456789 0123456789 0122222345678901234567 89 0123456789 012345678
                     AB                                       ABC
Chicken GL GIDN-TGRYTGY GSAVKGRATI SRDNGQSTVR LQLNNLRAEDTGT YYCAKAAG-
mh-C1      GISS-SGRYTNY GAAVKGRATI SRDNGQSTVR MQLNNLRAEDTAT YYCTRDSCN
mh-E1      GIGS-TGRCIGY GSAVKGRATI SRDNGQSTVR LQLNNLRPEDTAT YYCAKESGT
h-B1       GIGS-TGRCTGY GSAVRGRATI SRDNGQSTVR LQLNNLRAEDTAT YYCAKESGS 1          1
          0000000000012345678 9 0123
          ABCDEFGHIJ
Chicken GL ----------TAGSIDAWGHGTEV IVSS
mh-C1      GCWYFDTADRIDAWGHGTEV IVAA
mh-E1      GCGWAIYR--IDAWGHGTEV IVAA
h-B1       GCGWAIYR--IDAWGHGTEV IVAA
```

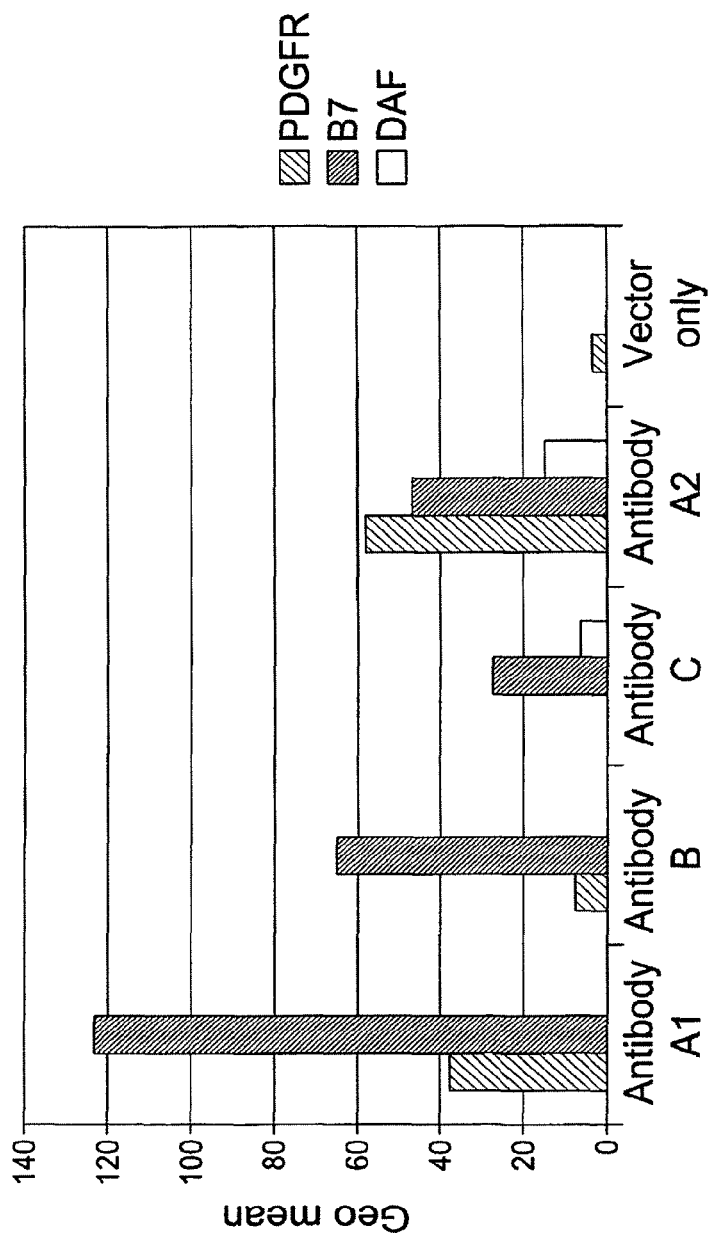

MAMMALIAN CELL-BASED IMMUNOGLOBULIN DISPLAY LIBRARIES

1. CROSS REFERENCE TO RELATED APPLICATIONS

This application claims benefit under 35 U.S.C. §119(e) to application Ser. No. 60/856,143, filed Nov. 1, 2006, the contents of which are incorporated herein by reference.

2. BACKGROUND

Hybridoma technology has been widely used to isolate antibodies for a variety of applications (Kohler and Milstein, 1975, Nature, 256, 495-7). Monoclonal antibodies have not only been indispensable as reagents but have also been developed as drugs to treat various human disease conditions including cancer, autoimmune, inflammatory and cardiovascular diseases, and viral infections (Reichert and Pavlou, 2004, Nat Rev Drug Discov, 3, 383-384). While the use of hybridoma technology to generate monoclonal antibodies is common practice in today's research and development laboratories, identification of the monoclonal antibodies that possess the desired binding and functional characteristics is a labor-intense, time-consuming process. This is largely due to the fact that hybridoma cells secrete, and are therefore disassociated from, the desired antibodies, thus making it an extensive and costly process to isolate the single hybridoma clones that secrete the antibody of interest.

The need for a rapid high-throughput screen of antibodies that specifically bind a specified target led to the development of cell surface display technologies in which the antibody-producing host cell remains physically associated with the displayed antibody of interest. This allows rapid isolation and sequence identification of the gene encoding the displayed antibodies having the desired binding characteristics. Such methods for identifying monoclonal antibodies include antibody display technologies using bacteria, yeast and ribosomes (Amstutz et al., 2001, Cliff Opin Biotechnol, 12, 400-405; Wittrup, 2001, Curr Opin Biotechnol, 12, 395-399).

Surface display technologies are also valuable for screening libraries of antibody fragments generated using variable domains isolated from diverse species immunized with the target antigen of interest. While the mouse is the most common source of monoclonal antibodies against human proteins, it is not always possible to raise high affinity antibodies against certain antigens or epitopes that are highly conserved between human and mouse, as such antigens have little or no immunogenicity in mice due to tolerance (Rajewsky, 1996, Nature, 381, 751-8). In such cases, immunization of non-rodent species, e.g. rabbit or chicken, is an alternative way to raise specific antibodies that bind a target of interest. DNA sequences encoding immunoglobulin variable domains are then generated from antibody-producing cells isolated from these immunized animals and cloned into a display library expression system.

In commonly used display library systems, antibodies are typically displayed as single chain Fv (scFv) or Fab fragments because the use of smaller sized fragments makes them amenable to phage display. Thus, characterization of the biological activities and further development of the isolated antibody fragments often requires conversion to whole immunoglobulins and expression in mammalian cells for proper folding and post-translational processing. This conversion process may produce antibodies with binding characteristics unlike those selected for in the initial screen.

We have developed a versatile mammalian expression vector that allows expression of membrane-bound and soluble forms of a selected immunoglobulin. The expression vectors described herein allow efficient conversion of full-length cell surface-bound immunoglobulins, which are used for the initial screening of specific binders, to the full-length secreted form of the selected binder immunoglobulin, which can be functionally characterized.

3. SUMMARY

Novel mammalian cell surface display vectors suitable for creating immunoglobulin display libraries for the identification and isolation of functional antibodies capable of binding a target antigen are described herein. The vectors are designed to enable the selection of high affinity antibodies, and subsequent isolation of the selected antibodies using mammalian cells. Antibodies isolated in this manner exhibit consistent and proper folding and post-translational modification. By restricting the entire process to mammalian cells, the antigen-binding characteristics of the isolated antibodies are not altered.

Compositions and methods using the mammalian cell surface display vector described herein have a number of advantages over existing display technologies and hybridoma technology. One advantage associated with the mammalian cell surface display technology described herein is that it combines the use of display technology to enrich for immunoglobulins having specific antigen binding with the biological characterization of immunoglobulins isolated using hybridoma technology. A second advantage is the use of the mammalian surface display vectors for the isolation and/or characterization of full-length monoclonal antibodies from any species, including species for which hybridoma technology is unavailable.

Accordingly, the compositions and methods described herein provide mammalian cell based immunoglobulin libraries that can be used in two distinct formats: (1) the expression of cell surface-bound immunoglobulins for affinity-based screening, and (2) the expression of secreted immunoglobulins for functional characterization. Furthermore, the expression vector comprises a replication origin that directs episomal propagation of the vector in the recombinant host cell. This allows rapid recovery of expression vector(s) encoding immunoglobulins having desired biological characteristics.

As described herein, the expression vectors are designed to allow easy and rapid conversion of the vector from one that directs expression of a membrane-bound immunoglobulin to a vector that directs expression of the secreted form of the same immunoglobulin. These expression vectors are referred to herein as "removable-tether display vectors," "transmembrane display vectors," or "TM-display vectors."

The removable-tether display vector typically comprises a first polynucleotide encoding an immunoglobulin heavy chain constant domain or an immunoglobulin light chain constant domain, a second polynucleotide encoding an immunoglobulin heavy chain constant domain or an immunoglobulin light chain constant domain, and a polynucleotide encoding a cell surface tether domain, wherein the polynucleotide encoding the cell surface tether domain is flanked by a first and a second restriction endonuclease site. In some embodiments, the polynucleotide encoding an immunoglobulin heavy chain constant domain is fused as its 3' end to a polynucleotide encoding the cell-surface tether domain. In some embodiments, when the first polynucleotide encodes an immunoglobulin heavy chain constant domain, the second polynucleotide encodes an immunoglobulin light chain constant domain. In some embodiments, when the first polynucleotide encodes an immunoglobulin light chain constant domain, the second polynucleotide encodes an immunoglobulin heavy chain constant domain. In some embodiments, the removable-tether display vector comprises a polylinker sequence.

In some embodiments, the removable-tether display vector comprises a first promoter operatively linked to the first or second polynucleotide encoding an immunoglobulin heavy chain constant domain or an immunoglobulin light chain constant domain. In some embodiments, the removable-tether display vector comprises a second promoter operatively linked to the first or second polynucleotide encoding an immunoglobulin heavy chain constant domain or an immunoglobulin light chain constant domain.

In some embodiments, the removable-tether display vector comprises an IRES element. In some embodiments the removable-tether display vector comprises an IRES element located between the first polynucleotide encoding an immunoglobulin heavy or light chain constant domain and the second polynucleotide encoding an immunoglobulin heavy or light chain constant domain. In some embodiments, the polynucleotides encoding the heavy chain constant domains are located downstream of the IRES element and the polynucleotide encoding the light chain constant domains are located upstream of the IRES element. In some embodiments, the polynucleotides encoding the light chain constant domains are located downstream of the IRES element and the polynucleotide encoding the heavy chain constant domains are located upstream of the IRES element.

In some embodiments, the first polynucleotide encoding an immunoglobulin heavy chain constant domain and/or the second polynucleotide encoding an immunoglobulin heavy chain constant domain comprises a polynucleotide encoding an immunoglobulin CH3 domain.

In some embodiments, the first polynucleotide encoding an immunoglobulin heavy chain constant domain and/or the second polynucleotide encoding an immunoglobulin heavy chain constant domain comprises a polynucleotide encoding immunoglobulin CH1, hinge, CH2 and CH3 domains.

In some embodiments, the removable-tether display vector comprises a polynucleotide encoding an immunoglobulin light chain variable domain. In some embodiments, the removable-tether display vector comprises a polynucleotide encoding an immunoglobulin heavy chain variable domain.

In some embodiments, the removable-tether display vector comprises a polynucleotide encoding a light chain variable domain or a heavy chain variable domain that is generated from vertebrates, including humans, primates, rodents (e.g., rat, mouse, hamster, guinea pig), and non-rodents, such as sheep, chicken, llama, cow, horse, pig, camel, dog, cat, rabbit, fish, and birds. In some embodiments, the removable-tether display vector comprises a polynucleotide encoding a light chain variable domain or a heavy chain variable domain that is generated from chicken.

In some embodiments, one or more amino acid residues encoded by the polynucleotide sequences encoding the heavy chain variable domain, the light chain variable domain, the heavy chain constant domain, the light chain constant domain, or combinations thereof, is mutated.

In some embodiments, the polynucleotides encoding the immunoglobulin heavy and light chain variable and constant domains are generated from genomic DNA. In some embodiments, the polynucleotides encoding the immunoglobulin heavy and light chain variable and constant domains are generated from cDNA.

In some embodiments of the removable-tether display vector, the cell-surface tether domain is platelet derived growth factor receptor (PDGF-R) transmembrane domain, B7-1 transmembrane domain or asialoglycoprotein receptor (AS-GPR). In some embodiments, the cell-surface tether domain is a GPI signal sequence which directs anchoring of the immunoglobulin to the cell-surface via a glycosidylphosphatidylinositol linker. In some embodiments, the GPI signal sequence is from human decay-accelerating factor (DAF). In some embodiments, the cell surface tether domain is from an immunoglobulin protein.

In some embodiments, the removable-tether display vector comprises a polynucleotide encoding a light chain constant domain that is either a lambda or kappa constant domain. In some embodiments, the light chain constant domain is a human light chain constant domain.

In some embodiments, the removable-tether display vector comprises a polynucleotide encoding a heavy chain constant domain wherein said constant domain is the mu constant chain domain, the delta constant chain domain, the gamma constant chain domain, the alpha chain domain, or the epsilon constant domain. In some embodiments, the gamma constant domain is selected from the gamma-1, gamma-2, gamma-3, and gamma-4 domain. In some embodiments, the heavy chain constant domain is a human heavy chain constant domain. In some embodiments, the removable-tether display vector comprises a polynucleotide encoding a heavy chain constant domain wherein the heavy chain constant domain is CH1, CH2, hinge, CH3, or CH4 or any combination thereof.

In some embodiments, the removable-tether display vector comprises: a polynucleotide encoding a first promoter, a polynucleotide encoding a drug resistance gene for selection of transfected eukaryotic cells, a polynucleotide encoding a second promoter, a restriction site for the insertion of a human light chain variable region, a polynucleotide encoding a light chain constant region, a polynucleotide encoding an internal ribosome entry site (IRES), a restriction site for the insertion of a human heavy chain variable region, a polynucleotide encoding a heavy chain constant region, a polynucleotide encoding a removable cell surface tether domain, a polynucleotide encoding a prokaryotic origin of replication, a polynucleotide encoding a drug resistance gene for selection of transformed prokaryotic cells, and a replication origin operative in a eukaryotic cell. In some embodiments, the replication origin is an Epstein-Barr virus replication origin. In some embodiments, the origin of replication is the EBV OriP sequence. In some embodiments, the removable-tether display vector comprises a polynucleotide encoding a replication factor. In some embodiments, the polynucleotide encoding a replication factor encodes an Epstein-Barr Nuclear Antigen 1 (EBNA-1) protein.

In some embodiments, the removable-tether display vector comprises a drug resistance gene for selection of transfected eukaryotic cells. In some embodiments, the drug resistance gene is a puromycin resistance gene, a neomycin resistance gene, a hygromycin gene, a xanthine-guanine phosphoribosyltransferase gene (gpt), a zeocin resistance gene, or a blasticidin resistance gene.

In some embodiments, the removable-tether display vector further comprises a drug resistance gene used for the selection of transformed prokaryotic cells. In some embodiments, the drug resistance gene used for selection of transformed prokaryotic cells is an ampicillin resistance gene, a kanamycin resistance gene, a tetracycline resistance gene, a cefotaxime resistant gene, a carbenicillin resistance gene, an actinomycin D resistance gene, a chloramphenicol resistance gene, or a streptomycin resistance gene.

In some embodiments, the first or second promoter of the removable-tether display vector is a simian virus 40 (SV40) early promoter, a SV40 late promoter, a mouse mammary tumor virus promoter, a human immunodeficiency virus long terminal repeat promoter, a moloney virus promoter, an avian leukemia virus promoter, an Epstein-Barr virus immediate early promoter, a Rous sarcoma virus promoter, a human action promoter, a human hemoglobin promoter, cytomegalovirus (CMV) promoter, a human EF-1 alpha promoter, or a human muscle creatine promoter.

In some embodiments, the removable-tether display vector comprises a polynucleotide encoding an origin of replication that functions in prokaryotic cells, a transcription terminator, and a polyadenylation signal. In some embodiments, the polynucleotide encoding the origin of replication that functions in prokaryotic cells is pBR, pUC, Col E1, p15A, Ori S, P1, or lambda. In some embodiments, the polynucleotide encoding the origin of replication that functions in prokaryotic cells is pBR.

In some embodiments, immunoglobulin display libraries are generated, wherein a plurality, or library, of antibody domain sequences are cloned into a given site within the display vector. In some embodiments, the removable-tether display vector comprises a library of polynucleotides encoding heavy and/or light chain variable domains. In some embodiments, the removable-tether display vector comprises a library of polynucleotides encoding heavy and/or light chain constant domains.

In some embodiments, the variable domains are generated from an antibody-producing cell isolated from any animal capable of producing antibodies upon immunization. In this embodiment, the target antigen can be used to immunize animals including but not limited to chicken, rabbit, llama, sheep, mouse, rat, hamster, non-human primate, or human. In some embodiments, variable domains are generated from naturally occurring antibody-producing cells that recognize the target antigen of interest and that are isolated from an animal. In some embodiments, the variable domains are derived from a humanized variable domain.

In some embodiments, a eukaryotic cell is transfected with the removable-tether display vector. In some embodiments, the eukaryotic cell is 293-HEK, HeLa, Jurkat, Raji, Daudi, COS, or CV-1 cells.

In some embodiments, a eukaryotic cell is transfected with the removable-tether display vector which lacks polynucleotides encoding replication factors and said eukaryotic cell is transfected with a second vector comprising a polynucleotide encoding a replication factor. In some embodiments, a eukaryotic cell which is transfected with the removable-tether display vector which lacks a polynucleotide encoding a replication factor further comprises a polynucleotide encoding a replication factor integrated in the genome of said eukaryotic cell. In some embodiments, replication factors can be provided form the host cell infected by the virus expressing viral replication factors.

In some embodiments is a eukaryotic cell comprising a first polynucleotide encoding an immunoglobulin heavy chain constant domain or an immunoglobulin light chain constant domain, a second polynucleotide encoding an immunoglobulin heavy chain constant domain or an immunoglobulin light chain constant domain, and a polynucleotide encoding a cell surface tether domain, wherein the polynucleotide encoding the cell surface tether domain is flanked by a first and a second restriction endonuclease site.

In some embodiments is a eukaryotic cell comprising a removable-tether display vector comprising an origin of replication, a first promoter operably linked to a first polynucleotide encoding an immunoglobulin heavy chain constant domain or an immunoglobulin light chain constant domain, a second polynucleotide encoding an immunoglobulin heavy chain constant domain or an immunoglobulin light chain constant domain, a polynucleotide encoding an immunoglobulin light chain variable domain, a polynucleotide encoding an immunoglobulin heavy chain variable domain, and a polynucleotide encoding a cell surface tether domain, wherein the polynucleotide encoding a cell surface tether domain is flanked by a first and a second restriction endonuclease recognition site. In some embodiments, the eukaryotic cell comprising a removable-tether display vector is 293-HEK, HeLa, Jurkat, Raji, Daudi, COS, or CV-1 cells.

In some embodiments, immunoglobulins comprising the heavy and light chain variable and constant domains are displayed on the surface of mammalian cells and screened for antigen binding affinity to a target antigen using methods including, but not limited to bead-based and/or fluorescence-activated cell sorting. In some embodiments, removable-tether display vectors encoding membrane-bound immunoglobulins having desired binding characteristics can be recovered from transfected cells and converted to an expression vector expressing the soluble form of the immunoglobulin via removal of the nucleic acid encoding the cell surface tether domain. In come embodiments, the soluble form of the immunoglobulin can be screened with labeled beads immobilized with antigen to detect the cells secreting specific antibodies (e.g., CellSpot™ (Trellis Bioscience, Inc., South San Francisco, Calif.)). In some embodiments, the soluble form of the immunoglobulin can be isolated and used to confirm antigen binding affinity and to characterize functional biological properties, such as antibody-dependent cellular cytotoxicity (ADCC), complement-dependent cytotoxicity (CDC), agonist or antagonist properties.

4. BRIEF DESCRIPTION OF THE FIGURES

FIG. 1A illustrates an exemplary embodiment of an immunoglobulin mammalian display vector.

FIG. 1B illustrates the mammalian display vector, pYA104, used to generate a chicken-human immunoglobulin library. Light chain regions=SEQ ID NOS:9 and 10; Heavy chain regions=SEQ ID NOS: 11 and 12.

FIGS. 2A-2F depict a fluorescence activated cell sorter analysis used to identify a chimeric immunoglobulin that binds IL-12.

FIG. 4A depicts the amino acid sequence of rearranged chicken anti-IL12 light chain VJ exons (SEQ ID NOS: 14-16) aligned with the germ line sequence (SEQ ID No: 13).

FIG. 4B depicts the amino acid sequence of rearranged chicken anti-IL12 heavy chain VDJ exons (SEQ ID NOS: 18-20) aligned with the germ line sequence (SEQ ID NO: 17).

FIG. 7 depicts FACS analysis of membrane-bound antibodies fused to various cell surface tether domains expressed on the surface of transfected cells.

5. DETAILED DESCRIPTION

5.2 Overview

Figure 1A:
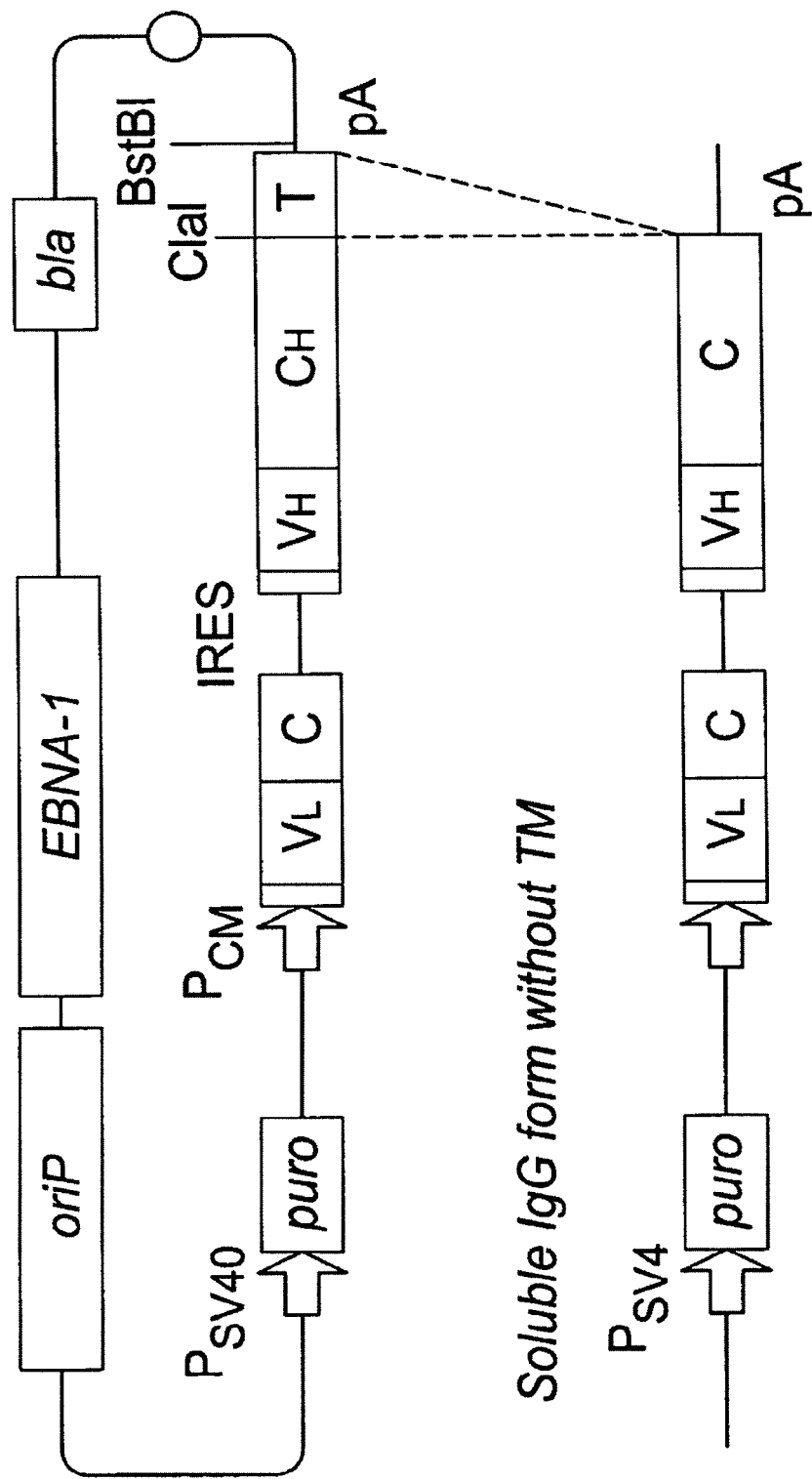

The compositions and methods described herein are useful for displaying immunoglobulins comprising heavy and light chain constant and variable domains. The expressed immunoglobulins are properly folded and post-translationally modified permitting the identification and isolation of immunoglobulins with desired antigen binding and functional characteristics. An advantage associated with the mammalian cell surface display systems described herein is the ability to display and characterize intact immunoglobulins. The ability to express and display intact immunoglobulins preserves the antigen-binding characteristics of the selected immunoglobulins. Another advantage of the invention is the ability to easily and rapidly recover the expression vector having the polynucleotide sequence encoding the immunoglobulin with desired binding activity. The ability to convert from membrane-bound to soluble forms of the immunoglobulin permits characterization of the functional biological properties of the immunoglobulin, including ADCC and CDC.

The mammalian immunoglobulin display vectors described herein comprise polynucleotide sequences encoding immunoglobulin heavy and light chain variable and constant domains. In some embodiments, an internal ribosome entry site (IRES) located between the polynucleotide sequences encoding the immunoglobulin light and heavy chains allows a single suitable eukaryotic promoter to control expression of both the immunoglobulin light and heavy chains as a single transcript. Polylinker sequences located 5' and adjacent to the polynucleotide sequences encoding the light and heavy chain constant domains allow the cloning of polynucleotide sequences encoding light and heavy variable domains upstream and in-frame with the polynucleotide sequences encoding the light and heavy chain constant domains, respectively. A polynucleotide sequence encoding a removable cell surface tether domain is located in-frame and 3' to the polynucleotide encoding the C-terminus of the heavy chain constant domain, allowing display of the expressed immunoglobulins on the surface of mammalian cells. The polynucleotide encoding the cell surface tether domain can be removed enzymatically, to enable conversion of the expressed immunoglobulin from a membrane-bound form to a soluble form Replication and stable maintenance of the vectors in mammalian cells is achieved by providing a viral origin of replication and one or more viral replication factors required for replication by a given viral origin of replication. Viral origins of replication and replication factors can be used from a variety of viruses, including Epstein-Barr virus (EBV), human and bovine papilloma viruses, and papovavirus BK. Stable maintenance of the vectors in an episomal form allow the easy and rapid isolation of removable-tether display vectors which encode immunoglobulins having desired binding properties.

5.3 Definitions

It is to be understood that both the foregoing general description and the following detailed description are exemplary and explanatory only and are not restrictive of the compositions and methods described herein. In this application, the use of the singular includes the plural unless specifically stated otherwise. Also, the use of "or" means "and/or" unless state otherwise. Similarly, "comprise," "comprises," "comprising," "include," "includes" and "including" are not intended to be limiting.

As used herein, the following terms and phrases are intended to have the following meanings:

The term "antigen" as used herein is defined as a molecule that provokes an immune response. This immune response may involve either antibody production, or the activation of specific immunologically-competent cells, or both. Antigens may be soluble substances, such as toxins and foreign proteins, or particulates, such as bacteria and tissue cells; however, only the portion of the protein or polysaccharide molecule known as the antigenic determinant (epitopes) combines with antibody or a specific receptor on a lymphocyte. Accordingly, any macromolecule, including virtually all proteins or peptides, can serve as an antigen. Antigens may also be small molecules such as amino acids or chemicals (haptens) or nucleic acids.

The term "cell surface antigen" is a cell-associated component that can behave as an antigen without disrupting the integrity of the membrane of the cell expressing the antigen.

The term "antibody" or "immunoglobulin" as used herein refers to a protein consisting of one or more polypeptides substantially encoded by immunoglobulin genes. The recognized immunoglobulin genes include the kappa, lambda, alpha, gamma (IgG1, IgG2, IgG3, IgG4), delta, epsilon and mu constant domain genes, as well as the myriad immunoglobulin variable (V) domain genes (as indicated below, there are V genes for both H-heavy- and L-light-chains).

The term "heavy chain" as used herein refers to the larger immunoglobulin subunit with associates with through its amino terminal region, with the immunoglobulin light chain. The heavy chain comprises a variable domain and a constant domain. The constant domain further comprises the CH1, hinge, CH2, and CH3 domains. In the case of IgE, IgM, and IgY, the heavy chain comprises a CH4 domain but does not have a hinge domain. The phrase "immunoglobulin heavy chain constant domain" refers to the CH1, hinge, CH2, CH3, CH4 domains or any combination thereof.

The term "light chain" as used herein refers to the smaller immunoglobulin subunit which associates with the amino terminal region of a heavy chain. As with a heavy chain, a light chain comprises a variable region and a constant region. There are two different kinds of light chains, kappa and lambda, referred to herein as "immunoglobulin light chain constant domains." A pair of these can associate with a pair of any of the various heavy chains to form an immunoglobulin molecule. Also encompassed in the meaning of light chain are light chains with a lambda variable region (V-lambda) linked to a kappa constant region (C-kappa) or a kappa variable region (V-kappa) linked to a lambda constant region (C-lambda).

A "chimeric antibody" as used herein is an antibody molecule in which (a) the constant region or domain, or a portion thereof, is altered, replaced, or exchanged so that the antigen binding site (variable region) is linked to a constant region of a different or altered class, and/or species, or an entirely different molecule which confers new properties to the chimeric antibody, e.g., an enzyme, toxin, hormone, growth factor, drug, effector function, chemoattractant, immune modulator, etc.; or (b) the variable region, or a portion thereof, is altered, replaced, or exchanged with a variable region having a different or altered antigen specificity.

The term "humanized antibody" or "humanized immunoglobulin" as used herein refers to an immunoglobulin comprising a human framework, at least one and preferably all complementarity determining regions (CDRs) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. See, e.g. Queen et al., U.S. Pat. Nos. 5,5301, 101; 5,585,089; 5,693,762; and 6,180,370; these and the other U.S. patents/patent applications are incorporated by reference in their entirety.

The term "epitope" as used herein refers to any portion (determinant) of a protein that is capable of eliciting an immune response and being specifically bound by an antibody. Epitope determinants usually consist of active surface groupings of molecules such as amino acids, and usually have specific three-dimensional structural characteristics, as well as specific charge characteristics. Two antibodies are said to bind to substantially the same epitope of a protein (or the overlapping epitope of a protein) if amino acid mutations in the protein that reduce or eliminate binding of one antibody also reduce or eliminate binding of the other antibody, and/or if the antibodies compete for binding to the protein, i.e., binding of one antibody to the protein reduces or eliminates binding of the other antibody. The determination of whether two antibodies bind substantially to the same epitope is accomplished by the methods known in the art, such as a competition assay. Sec for example, Harlow et al., Eds., Antibodies: A Laboratory Manual, Chapter 14, Cold Spring Harbor Laboratory, Cold Spring Harbor (1988) and Munson et al., Anal. Biochem., 107, 220-239 (1980).

"Nucleic acid" or "oligonucleotide" or "polynucleotide" or grammatical equivalents as used herein means at least two nucleotides covalently linked together. Oligonucleotides are typically from about 5, 6, 7, 8, 9, 10, 12, 15, 25, 30, 40, 50, or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have at least one different linkage, e.g., phosphoramidate, phosphorothioate, phosphorodithioate, or O-methylphosphoroamidite linkages (see Eckstein (1992) Oligonucleotides and Analogues: A Practical Approach Oxford Univ. Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7 of Sanghvi and Cook (eds. 1994) Carbohydrate Modifications in Antisense Research ACS Symposium Series 580. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. The depiction of a single strand also defines the sequence of the complementary strand; thus the sequences described herein also provide the complement of the sequence. The nucleic acid may be DNA, both genomic and cDNA, RNA, or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g., the individual units of a peptide nucleic acid, each containing a base, are referred to herein as a nucleoside.

The term "polylinker" as used herein is a nucleic acid sequence that comprises a series of two or more different restriction endonuclease recognition sequences closely spaced to one another (i.e. less than 10 nucleotides between each site).

The terms "polypeptide," "peptide," and "protein," are used interchangeably herein to refer to a polymer of amino acid residues. The terms apply to amino acid polymers in which one or more amino acid residues is an artificial chemical mimetic of a corresponding naturally occurring amino acid, as well as to naturally occurring amino acid polymers, those containing modified residues, and non-naturally occurring amino acid polymers.

The term "amino acid" as used herein refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain some basic chemical structure as a naturally occurring amino acid. Amino acid mimetic refers to a chemical compound that has a structure that is different from the general chemical structure of an amino acid, but that functions similarly to another amino acid.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

The term "recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed, or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, e.g., using the in vivo cellular machinery of the host cell rather than in vitro manipulations; however, such nucleic acids, once produced recombinantly, although subsequently replicated non-recombinantly, are still considered recombinant for the purposes of the invention.

The term "recombinant protein" is a protein made using recombinant techniques, e.g., through the expression of a recombinant nucleic acid as depicted above. A recombinant protein is distinguished from naturally occurring protein by at least one or more characteristics. The protein may be isolated or purified away from some or most of the proteins and compounds with which it is normally associated in its wild type host, and thus may be substantially pure. An isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a recombinant protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

The term "heterologous" when used with reference to portions of a nucleic acid indicates that the nucleic acid comprises two or more subsequences that are not normally found in the same relationship to each other. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other, e.g., a fusion protein.

A "promoter" is typically an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is active under environmental or developmental regulation. "Operably linked" refers to a juxtaposition of two or more components, wherein the components so described are in a relationship permitting them to function in their intended manner. For example, a promoter and/or enhancer is operably linked to a coding sequence if it acts in cis to control or modulate the transcription of the linked sequence. Generally, but not necessarily, the DNA sequences that are "operably linked" are contiguous and, where necessary to join two protein coding regions or in the case of a secretory leader, contiguous and in reading frame. However, although an operably linked promoter is generally located upstream of the coding sequence, it is not necessarily contiguous with it. A polyadenylation site is operably linked to a coding sequence if it is located at the downstream end of the coding sequence such that transcription proceeds through the coding sequence into the polyadenylation sequence. Linking is accomplished by recombinant methods known in the art, e.g., using PCR methodology, by annealing, or by ligation at convenient restriction sites. If convenient restriction sites do not exist, then synthetic oligonucleotide adaptors or linkers are used in accord with conventional practice.

The term "transfected" or "transformed" or "transduced" as used herein refers to a process by which exogenous nucleic acid is transferred or introduced into the host cell. A transformed cell includes the primary subject cell and its progeny.

The term "library" as used herein, refers to a diverse collection or population of nucleic acids that encode polypeptides, wherein the polypeptide sequences are different in the combination of amino acids that are introduced into these sequences.

A "membrane-bound protein" or "membrane-localized protein" as used herein, refers to a protein that is associated to the external face of the host cell. A membrane-bound protein may be associated with the external face of the host cell either via a transmembrane domain or a domain containing a lipid anchor, such as a GPI linker domain.

A "cell surface tether domain" as used herein, refers to an amino acid sequence that confers the ability of a polypeptide to be associated with a host cell outer membrane, and which is sometimes but not always naturally present in the protein of interest. As described herein, cell surface tether domains include, for example, transmembrane domains or glycosidylphosphatidylinositol (GPI) signal sequences. GPI signal sequences can be recognized as described in Udenfriend and Kodukula (1995), Methods Enzymol. 250:571-582. In the present invention, it is understood that GPI signal sequences specify a processing event in the cell that results in cleavage and removal of the GPI signal domain and covalent attachment of a GPI anchor to the new C-terminus of the protein. In the case of DAF, the last about 30-50 residues of DAF contain a signal that directs a processing event in cells in which the last about 28 residues are proteolytically removed and replaced with a hydrophobic glycolipid (GPI) that acts as a membrane anchor. Transmembrane domains can be predicted as described by Sonnhamer et al. (1998), Proc. of ISMB 6:175-182. Transmembrane domains and GPI anchor sequences that can be recognized as described above are membrane association sequences as meant herein. A protein comprising a membrane association sequence may, in many cases, be associated with the cell surface, particularly if the protein also comprises a signal sequence in its precursor form (see discussion of "signal sequence" below). Association of a protein with a cell surface can be determined by fluorescence activated cell sorting (FACS) analysis using non-permeabilized cells that express the protein. FACS is described in, e.g., Current Protocols in Cytometry, Robinson et al., eds., John Wiley & Sons (2004); Edidin (1989), Methods in Cell Biology 29:87-102.

The term "expression vector" as used herein refers to a self-replicating polynucleotide and, in the present invention, comprises an expression construct. The expression vector will comprise at least one replication origin (also referred to as "origin of replication"). The replication origin confers the ability to replicate in a host and may be viral, eukaryotic, or prokaryotic. The expression vector may be used to stably or transiently transfect a eukaryotic cell line or may be used in transformation of a prokaryotic cell. The expression vector may exist extra-chromosomally in a transient transfectant. In a stable transfectant, the expression vector may be propagated as an episomal vector or may be integrated into the host cell chromosome. The expression vector of the present invention may further comprise at least one selectable marker gene to facilitate recognition of either prokaryotic or eukaryotic transfectants. An expression vector, as used herein, may contain both a eukaryotic and a prokaryotic origin of replication.

The term "signal peptide" as used herein refers to a hydrophobic sequence that mediates insertion of the protein through the membrane bounding the ER. Type I transmembrane proteins also comprise signal sequences. "Signal sequences," as used herein are amino-terminal hydrophobic sequences which are usually enzymatically removed following the insertion of part or all of the protein through the ER membrane into the lumen of the ER. Thus, it is known in the art that a signal precursor form of a sequence can be present as part of a precursor form of a protein, but will generally be absent from the mature form of the protein. When a protein is said to comprise a signal sequence, it is to be understood that, although a precursor form of the protein does contain the signal sequence, a mature form of the protein will likely not contain the signal sequence. Examples of signal peptides or sequences that are functional in mammalian host cells include the following: the signal sequence for interleukin-7 (IL-7) described in U.S. Pat. No. 4,965,195; the signal sequence for interleukin-2 receptor described in Cosman et al. ((1984), Nature 312:768); the interleukin-4 receptor signal peptide described in EP Patent No. 0 367 566; the type I interleukin-1 receptor signal sequence described in U.S. Pat. No. 4,968,607; the type II interleukin-1 receptor signal peptide described in EP Patent No. 0 460 846; the signal sequence of human IgG (which is METDTLLLWVLLLWVPGSTG; SEQ ID NO:21); and the signal sequence of human growth hormone (MATGSRTSLLLAFGLLCLPWLQEGSA; SEQ ID NO:22). Many other signal sequences are known in the art. In some embodiments, the signal peptide may be the naturally occurring signal peptide for a protein of interest or it may be a heterologous signal peptide.

5.4 Removable-Tether Display Vectors

Removable-tether display vectors typically comprise a self-replicating origin of replication, at least one eukaryotic promoter, a nucleic acid encoding a removable cell surface tether domain, a nucleic acid encoding an immunoglobulin constant domain, polylinkers for the insertion of polynucleotides encoding immunoglobulin light and heavy chain variable regions upstream of the immunoglobulins encoding light and heavy chain constant regions, respectively, an internal ribosome entry site (IRES), and at least one selectable marker. In addition, the vectors can comprise a prokaryotic origin of replication, a transcriptional terminator, a polyadenylation signal and/or leader sequences, as well as other sequences necessary for expression in eukaryotic host cells. Removable-tether display vectors are also referred to herein as "transmembrane and display vectors," "TM-display vectors," or "mammalian immunoglobulin display vectors."

5.4.1 Removable Cell Surface Tether Domains

In some embodiments, the removable-tether display vector comprises a polynucleotide encoding a cell surface tether domain. The cell surface tether domains used to display tetrameric immunoglobulin molecules on the cell surface can be any peptide domain that causes the immunoglobulin to which the cell surface tether domain is fused to be anchored to the cell surface of the recombinant host cell. Essentially any transmembrane domain is compatible with the vectors described herein. Transmembrane domains include, but are not limited to: a member of the tumor necrosis factor receptor superfamily, CD30, platelet derived growth factor receptor (PDGFR, e.g. amino acids 514-562 of human PDGFR; Chestnut et al., 1996, J Immunological Methods, 193:17-27; also see Gronwald et al., 1988, PNAS, 85:3435-3439); nerve growth factor receptor, Murine B7-1 (Freeman et al., 1991, J Exp Med 174:625-631), asialoglycoprotein receptor H1 subunit (ASGPR; Speiss et al. 1985 J Biol Chem 260:1979-1982), CD27, CD40, CD120a, CD120b, CD80 (B7) (Freeman et al., 1989, J Immunol, 143:2714-2272) lymphotoxin beta receptor, galactosyltransferase (e.g., GenBank accession number AF155582), sialyltransferase (E.G. GenBank accession number NM_003032), aspartyl transferase 1 (Asp1; e.g. GenBank accession number AF200342), aspartyl transferase 2 (Asp2; e.g. GenBank accession number NM_012104), syntaxin 6 (e.g. GenBank accession number NM-005819), ubiquitin, dopamine receptor, insulin B chain, acetylglucosaminyl transferase (e.g. GenBank accession number NM_002406), APP (e.g. GenBank accession number A33292), a G-protein coupled receptor, thrombomodulin (Suzuki et al., 1987, EMBO J, 6:1891-1897) and TRAIL receptor.

In some embodiments, the transmembrane domain is from a human protein. All or part of a transmembrane domain from a protein may be utilized in the vectors described herein.

In some embodiments, a cell surface displayed antibody or fragment thereof comprises the transmembrane domain of human platelet derived growth factor receptor (PDGF-R) having the amino acid sequence AVGQDTQEVIVVPH-SLPFKVVVISAILALVVLTIISLIILIMLWQKKPR (SEQ ID NO:4), fused to the C-terminus of the CH3 domain of the immunoglobulin heavy chain protein. The encoding nucleic acid sequence is disclosed herein as SEQ ID NO:3.

In some embodiments, a cell surface displayed antibody or fragment thereof of the current invention comprises the transmembrane domain of the B7-1 (CD80) protein having the amino acid sequence KPPEDPPDSKNTLVLFGAGFGAV-ITVVVIVVIIKCFCKHRSCFRRNEASRETNNSLT FGPEEALAEQTVFL (SEQ ID NO:6). The encoding nucleic acid sequence is disclosed herein as SEQ ID NO:5.

In some embodiments, the cell surface tether domain may be a GPI (glycosidylphosphatidylinositol) signal domain that specifies a processing event in the cell that results in cleavage and removal of the 29-37 residue GPI signal domain, and covalent attachment of a GPI anchor to the new C-terminus of the protein. In some embodiments, the GPI signal domain has the amino acid sequence PNKGSGTTSGTTRLLS-GHTCFTLTGLLGTLVTMGLLT (SEQ ID NO:2). The encoding nucleic acid sequence is disclosed herein as SEQ ID NO:1.

It will be understood that "GPI-linked" when used in reference to expressed proteins of interest refers to the post-translationally modified fusion. For example, an immunoglobulin that is ordinarily secreted will be produced in the recombinant cell culture as a C-terminal fusion of the preprotein with the GPI signal domain. Rather than being secreted, this fusion will become GPI-linked during processing and will be transported to the cell membrane and remain lodged there by virtue of the GPI anchor.

Several proteins are known that contain the C-terminal domains substituted with phospholipids anchors. Such proteins include Thy-1 (Low et al., Nature (London), 1985, 318: 62-64 and Tse et al., 1985, Science, 230:1003-1008), the variant surface glycoproteins (VSGs) of African trypanosomes (Ferguson et al., 1985, J. Biol. Chem. 260:14547-14555), acetylcholinesterase (Futerman et al., 1985, Biochem. J., 226:369-377), 5' nucleotidase (Low et al., 1978, Biochim. Biophys. Acta 508:565-570), and DAF (Davitz et al., 1986, J. Exp. Med. 163:1150-1161) and Medof et al., 1986, Biochemistry 25:6740-6747). Attachment of the DAF anchor, which contains glycosylated phosphatidylinositol (PI) and ethanolamine, apparently occurs following proteolytic removal of 17-31 C-terminal residues from mDAF (Low, M. G., 1987, Biochem J., 244:1-13 and Cross, G. A. M., 1987, Cell 48:179-181).

One skilled in the art can adapt the method performed in Chou et al. 1999, Proteins, 34:137-153 to optimize or screen different transmembrane domains and/or GPI-anchor domains for use in the vectors described herein.

In some embodiments, the polynucleotide encoding a removable cell surface tether domain is fused in-frame and adjacent to the 3' end of a polynucleotide encoding an immunoglobulin heavy chain constant domain, and is flanked by restriction endonuclease recognition sites that generate compatible ends when digested by said endonucleases. The polynucleotide encoding the removable cell surface tether domain provides a rapid and efficient method of converting a removable-tether expression vector from one encoding a membrane-bound immunoglobulin to one encoding a secreted immunoglobulin.

Expression vector DNA is isolated from recombinant host cells that have been selected as expressing membrane-bound immunoglobulins with desired antigen binding specificity and/or affinity. Using methods known to those skilled in the art, appropriate endonucleases are used to remove the nucleic acid encoding the removable cell surface tether domain. The free ends of the digested vector are ligated to form a vector that expresses the soluble form of the desired immunoglobulin. The vector lacking the polynucleotide encoding the cell surface tether domain can be used to transfect host cells to produce secreted immunoglobulin.

FIG. 1A illustrates an exemplary embodiment in which the polynucleotide encoding the cell surface tether domain is designed to be removable by digestion with ClaI and BstBI for the efficient conversion between membrane-bound and soluble immunoglobulin molecules. Fusion of the polynucleotide encoding the cell surface tether domain to the 3' terminus of the polynucleotide encoding the heavy chain constant region allows the immunoglobulins to be displayed on the cell surface without loss of their antigen-binding characteristics. The ability to remove the polynucleotide encoding the cell surface tether domain allows the conversion of the membrane-bound immunoglobulin to a soluble form, allowing the use of affinity binding assays and biological assays to characterize the functional properties of the isolated immunoglobulins. Although the vector in FIG. 1A uses ClaI and BstBI, other restriction endonucleases can also be used, provided that the restriction endonucleases produce compatible ends. Examples of pairs of enzymes that can be used to produce compatible ends include, but are not limited to, BamHI/BglII, XhoI/SalI, NgoMIV/PinAI/BspEI, and NheI/SpeI/XbaI. Endonucleases that generate blunt ends are also considered to produce compatible ends for the purpose of the invention described herein.

5.4.2 Immunoglobulin Domains

The mammalian display vectors described herein are typically used to display intact antibodies, although antibody fragments, e.g., Fc, Fab', F(ab)'$_2$, and single chain Fv, can also be displayed. Generally, each light chain and each heavy chain is encoded in a separate transcriptional unit, or gene. The recognized immunoglobulin genes include the kappa and lambda light chain constant region genes, the alpha, gamma (IgG1, IgG2, IgG3, IgG4), delta, epsilon and mu heavy chain constant region genes, and immunoglobulin variable region genes. The polynucleotides used in the mammalian display vectors can encode any of the recognized immunoglobulin genes, as well as immunoglobulin variable V region genes Examples of suitable sources for immunoglobulin genes include, but are not limited to, humans, primates, rodents (e.g., rat, mouse, hamster, guinea pig), turkey, quail, trout, shark, camel and non-rodents, such as sheep, chicken, llama and rabbit. In addition to immunoglobulins obtained from various organisms, variant forms of known antibodies can be used, including humanized, chimeric and monoclonal antibodies. Methods of obtaining polynucleotide encoding immunoglobulin variable domains are well known in the art and include PCR-amplification and sub-cloning.

In some embodiments, the light and heavy chain variable regions can be from one species and the light and heavy chain constant region from another species. For example, the variable chain regions can be from an avian species, such as chicken, while the constant chain regions can be from human. By way of another example, the variable chain region can be from human and the light chain can be from rodent. By way of another example, the variable and constant chain regions can be from different rodents, i.e., the variable chain regions can be from rat and the constant chain regions from mouse. In other embodiments, the light and heavy chain constant and variable regions can be from the same species, such as human.

In some embodiments, a polynucleotide encoding an immunoglobulin light chain variable domain is cloned into the restriction endonuclease site juxtaposed to the polynucleotide encoding the light chain constant domain and a polynucleotide encoding an immunoglobulin heavy chain variable domain is cloned into the polylinker site juxtaposed to the polynucleotide encoding the heavy chain constant domain.

In some embodiments, a polynucleotide encoding an immunoglobulin light chain constant domain is cloned into a restriction endonuclease site juxtaposed to the polynucleotide encoding the light chain variable domain and/or a polynucleotide encoding an immunoglobulin heavy chain constant domain is cloned into a restriction endonuclease site juxtaposed to the polynucleotide encoding the heavy chain variable domain. Cloning of the DNA sequence encoding the variable domain gene may be done according to the methods found in Co et al. (J. Immunology; 148:1149 (1992). In some embodiments, the variable domain cDNAs are cloned by an anchored PCR method, using as a template cDNA which was generated by a reverse transcriptase reaction that added a 5' G-tail and restriction site. The variable domain cDNA can then be cloned using a 5' PCR primer which can anneal to the G-tail and restriction site, and a 3' PCR primer that anneals to kappa light chain sequence.

In some embodiments, polynucleotide sequences encoding heavy and light chain constant domains are cloned from mRNA expressed by antibody-producing cells. In other embodiments, polynucleotide sequences encoding heavy and light chain constant domains are cloned from genomic DNA.

The cloning sites for the heavy and light chain constant and variable regions can be flanked by symmetrical or non-symmetrical restriction endonuclease recognition sequences. By "symmetrical" herein is meant that the restriction endonuclease cleaves within a palindromic DNA sequence. Accordingly, in some embodiments, the heavy and light chain constant and variable regions are flanked by symmetrical restriction endonuclease recognition sequences. Typically, the cloning sites on either side of the heavy and light chain constant and variable regions comprise two different restriction endonuclease recognition sequences. Examples of suitable pairs of restriction endonucleases for use in the compositions and methods described herein include, but are not limited to, NgoMIV/NotI, NotI/XhoI, and NgoMIV/SacI.

In some embodiments, non-symmetrical restriction endonuclease recognition sites are used for the insertion of heavy and light chain constant and variable regions. "Non-symmetrical restriction endonuclease recognition sequences" are sequences that are not identical to each other, but that can be cleaved by the same restriction endonuclease, such that the single-stranded ends formed by cleaving both restriction endonuclease recognition sequences with the same restriction endonuclease are neither complementary to each other nor self-complementary. Examples of non-symmetrical restriction endonuclease recognition sequences that can be used in the compositions and methods described herein include BstXI and SfiI (see, e.g., U.S. Pat. No. 5,595,895; the content of which is incorporated herein by reference in its entirety).

In the exemplary embodiment illustrated in FIG. 1B, the vector comprises symmetrical and non-symmetrical restriction endonuclease sites for the cloning the light and heavy chain variable regions. As illustrated in FIG. 1B, the light chain variable region is flanked by non-symmetrical restriction endonuclease sites for the restriction endonuclease SfiI, while the heavy chain variable region is flanked by symmetrical restriction endonculease sites for NgoMIV and NotI.

5.4.3 Internal Ribosome Entry Sites (IRES Elements)

IRES sequences can be used to produce multicistronic transcripts which include coding sequences for multiple proteins. These coding sequences may encode the same protein, or different proteins e.g., the heavy and light chains of an antibody. By including coding sequences for multiple proteins in a single transcript, equivalent expression levels for the proteins can be obtained. IRES sequences can be incorporated in expression vectors to produce subunits of a molecular complex from a single transcriptional unit, or to readily incorporate selectable and/or scorable reporters into exchangeable segments without creating fusion proteins or the use of additional regulatory elements to control expression of the second gene.

Examples include those IRES elements from poliovirus Type I, the 5'UTR of encephalomyocarditis virus (EMV), of "Thelier's murine encephalomyelitis virus (TMEV) of "foot and mouth disease virus" (FMDV) of "bovine enterovirus (BEV), of "coxsackie B virus" (CBV), or of "human rhinovirus" (HRV), or the "human immunoglobulin heavy chain binding protein" (BIP) 5'UTR, the *Drosophila* antennapediae 5'UTR or the *Drosophila* ultrabithorax 5'UTR, or genetic hybrids or fragments from the above-listed sequences. IRES sequences are described in Kim, et al., 1992, Molecular and Cellular Biology 12:3636-3.643 and McBratney, et al., 1993, Current Opinion in Cell Biology 5:961-965.

In some embodiments, an IRES element is positioned between the polynucleotide encoding the immunoglobulin heavy chain and the polynucleotide encoding the immunoglobulin light chain. As illustrated in FIG. 1A, both heavy and light chains are encoded as a single transcript by virtue of the use of an internal ribosome entry site (IRES) element, which joins the polynucleotide sequence encoding the variable and constant light chains to the polynucleotide encoding the variable and constant heavy chains.

In some embodiments, the polynucleotide sequences encoding the immunoglobulin light chain variable and constant domains can be located upstream of the IRES element and the polynucleotide sequences encoding the immunoglobulin heavy chain variable and constant domains can be located downstream of the IRES element. In other embodiments, the polynucleotide sequences encoding the immunoglobulin heavy chain variable and constant domains can be located upstream of the IRES element and the polynucleotide sequences encoding the immunoglobulin light chain variable and constant domains can be located downstream of the IRES element.

In some embodiments, the removable-tether domain vector comprises a first promoter operably linked to a polynucleotide sequence encoding the immunoglobulin light chain variable and constant domains, and further comprises a second promoter operably linked to a polynucleotide encoding the immunoglobulin heavy chain variable and constant domains.

5.4.4 Self-Replicating Vector Elements

The removable-tether display vectors can be linear or circular, single or double-stranded. The vectors are generally within the size range of 1 kb-100 kb, but typically are between 1 to 10 kb, 10 to 20 kb, 20 to 30 kb, 30 to 40 kb, 40 to 50 kb, 50 to 60 kb, 60 to 70 kb, 70 to 80 kb, 80 to 90 kb, and 90 to 100 kb.

The removable-tether display vectors for use in the compositions and methods described herein typically comprise a portion of a virus genomic DNA or cDNA that encodes an origin of replication (ori) required for the vectors to be self-replicating. In addition, the vectors can contain one or more genes encoding viral proteins that are required for replication, i.e., replication factors. In some embodiments, the replication factors can be expressed in trans on another vector in the cell or from the genomic DNA of the host cell. In some embodiments, the replication factors can be encoded by a viral genome that is maintained in a episomal state in the host cell.

In some embodiments, the viral origin of replication is the oriP of Epstein-Barr virus (EBV) and the replication protein factor is the trans-acting EBNA-1 protein or a variant thereof. EBNA-1 can be expressed on the episomal display vector carrying oriP, on another vector present in the cell, or from an EBNA-1 gene in the genomic DNA of the host cell. The oriP from EBV is described in Yates et al., 1985, Nature, 313, 812-815, Sugden et al., 1985, Mol Cell Biol, 5, 410-413, Margolskee et al., 1988, Mol Cell Biol, 8, 2837-2847, and in Chittenden et al., 1989 J Virol, 63, 3016-3025. An EBV-based episomal vector suitable for use in the compositions and methods described herein comprising the OriP region of EBV and the EBNA-1 gene of EBV is illustrated in FIG. 1A.

In some embodiments, the removable-tether display vectors comprise the replication functions of the papilloma family of viruses, including but not limited to Bovine Papilloma Virus (BPV) and Human Papilloma Virus (HPVs). BPV and HPVs persist as stably maintained plasmids in mammalian cells. Two trans-acting factors encoded by BPV and HPV, namely E1 and E2, or variants thereof are sufficient for supporting replication in many mammalian cells (Ustav et al., 1991, EMBO J, 10, 449-457, Ustav et al., 1991, EMBO J, 10, 4231-4329, Ustav et al., 1993, Proc Natl Acad Sci USA, 90, 898-902, Piirsoo et al., 1996, EMBO J, 15, 1-11, and PCT Publication WO 94/12629.

In some embodiments, the removable-tether display vectors can be derived from a human papovavirus BK genomic DNA molecule. For example, the BK viral genome can be digested with restriction endonucleases EcoRI and BamHI to produce a fragment that contains the BK viral origin of replication sequences that can confer stable maintenance on vectors (see, for example, De Benedetti and Rhoads, 1991, Nucleic Acids Res, 19:1925-1931), as can a 3.2 kb fragment of the BK virus (Cooper and Miron, 1993, Human Gene Therapy, 4:557-566).

For propagation and/or use in prokaryotic host cells, the vectors also include a prokaryotic origin of replication. Prokaryotic origins of replication suitable for use in the compositions and methods described herein include, but are not limited to, pUC, Col E1, p15A, Ori S, lambda, and/or P1.

5.4.5 Promoters

Typically, the removable-tether display vectors include one or more promoters and/or enhancers capable of directing the expression of the polynucleotide sequences in the various cell types used in the compositions and methods described herein.

The promoters can be constitutive, tissue-specific, inducible, and/or useful under the appropriate conditions to direct expression of the introduced polynucleotide sequence(s). The promoters can be heterologous or endogenous. Promoters suitable for use in compositions and methods described herein include, but are not limited to, the cytomegalovirus (CMV) promoter, the simian virus 40 (SV40) early or late promoters, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, the actin promoter, the myosin promoter, the hemoglobin promoter, the EF-1 alpha promoter, and/or the muscle creatine promoter.

FIG. 1A illustrates an exemplary embodiment in which two promoters, SV40 and CMV, are included in the removable-tether display vector. In the embodiment illustrated in FIG. 1A, the SV40 promoter is used to direct the expression of a polynucleotide sequence encoding the puromycin drug resistance gene. The CMV promoter is used to direct the expression of the immunoglobulin light and heavy chains.

5.4.6 Selectable Markers

The inclusion of one or more polynucleotides encoding selectable markers aids in the identification of transformants. Typical selection genes encode proteins that (a) confer resistance to antibiotics or other toxins, (b) complement auxotrophic deficiencies, or (c) supply critical nutrients not available from complex media, e.g., the gene encoding D-alanine racemase for Bacilli.

Exemplary selection systems include, but are not limited to, the herpes simplex virus thymidine kinase (Wigler, et al., 1977, Cell 11:223-232), hypoxanthine-guanine phosphoribosyltransferase (Szybalska & Szybalski, 1962, Proc. Natl. Acad. Sci. USA 48:2026-2034), and adenine phosphoribosyltransferase (Lowy et al., 1980, Cell 22:817-823) genes can be employed in tk⁻, hgprt⁻ or aprt cells, respectively. Also, antimetabolite resistance can be used as the basis of selection for dhfr, which confers resistance to methotrexate (Wigler et al., 1980, Proc. Natl. Acad. Sci. USA 77:3567-3570; O'Hare et al., 1981, Proc. Natl. Acad. Sci. USA 78:1527-1531); gpt, which confers resistance to mycophenolic acid (Mulligan & Berg, 1981, Proc. Natl. Acad. Sci. USA 78:2072-2076); neo, which confers resistance to the aminoglycoside G-418 (Colberre-Garapin et al., 1981, J. Mol. Biol. 150:1-14); hygro, which confers resistance to hygromycin genes (Santerre, et al., 1984, Gene 30:147-156); neomycin resistance (neo), hypoxanthine phosphoribosyl transferase (HPRT), puromycin (puro), dihydro-orotase glutamine synthetase (GS), carbamyl phosphate synthase (CAD), multidrug resistance 1 (mdr1), aspartate transcarbamylase, adenosine deaminase (ada), and blast, which confers resistance to the antibiotic blasticidin.

Additional selectable genes that can be used in the compositions and methods described herein also include, trpB, which allows cells to utilize indole in place of tryptophan; hisD, which allows cells to utilize histinol in place of histidine (Hartman & Mulligan, 1988, Proc. Natl. Acad. Sci. USA 85:8047-8051); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.). The use of visible reporters has gained popularity with such reporters as anthocyanins, β glucuronidase and its substrate GUS, luciferase and its substrate luciferin. Green fluorescent proteins (GFP) (Clontech, Palo Alto, Calif.) and related derivatives such as Yellow Fluorescent Protein (YFP) and Emerald Green Fluorescent Protein (EmGFP) (Invitrogen Corporation, Carlsbad, Calif.) can be used as both selectable reporters (see, e.g., Chalfie, M. et al., 1994, Science, 263:802-805) and homeostatic scorable reporters (see, e.g., Rhodes, C. A. et al., 1995, Methods Mol. Biol., 55:121-131).

In other embodiments, the vectors can comprise one or more genes conferring resistance to both eukaryotic and prokaryotic cells. For example, zeocin resistance can be used to select both eukaryotic and prokaryotic cells.

In other embodiments, the vectors can comprise a gene conferring resistance to a eukarytoic cell and a gene conferring resistance to a prokaryotic cell. The exemplary vector illustrated in FIG. 1A includes the puromycin resistance gene to identify transformed eukaryotic cells and the ampicillin (bla) resistance gene to identify transformed prokaryotic cells.

5.4.7 Additional Elements.

Additional elements that can be included in the expression vectors are sequences necessary for expression in eukaryotic host cells, including but not limited to, yeast, fungi, insect, plant, animal, human or nucleated cells from other muticellular organisms, the display vectors contain sequences necessary for expression in the chosen eukaryotic host cells. Examples of such sequences include sequences encoding polyadenylation signals, termination of transcription, stabilization of mRNA, and/or leader sequences. Such sequences are commonly available from the 5' and, occasionally 3' untranslated regions of eukaryotic or viral DNAs or cDNAs. See also U.S. Patent Publication 2004/0115814, the content of which is incorporated herein by reference in its entirety.

An exemplary removable-tether display vector is illustrated in FIG. 1B. To facilitate the isolation of antibodies with desired binding characteristics and biological activities, the removable-tether display vector depicted in FIG. 1B comprises a nucleotide encoding a removable GPI signal domain fused to the C-terminus of the heavy chain constant region. When present, the GPI signal domain enables immunoglobulin molecules to be displayed on the surface of the mammalian host cell. Both light and heavy chains are produced as a single transcript with the aid of the IRES under the control of the CMV promoter. Removal of the nucleotide encoding the GPI signal sequence by digestion with ClaI and BstBI, allows conversion from membrane-bound to soluble immunoglobulin molecules. The vector contains the EBV replication origin (oriP) and nuclear antigen-1 (EBNA-1) gene to support plasmid replication in mammalian cells. The immunoglobulin display vector also includes polynucleotide sequences encoding a bacterial replication origin (pUC ori), transcription terminator (tt), polyadenylation signal (p(A)), and signal peptides for light and heavy chain constant region (represented as thick lines). Although the mammalian surface display vector pYA104, depicted in FIG. 1B, includes the immunoglobulin gene encoding the human heavy chain constant region $IgG_1$, the vector can readily be used to express different isotypes or species of antibodies.

5.5 Methods for Selecting Immunoglobulins with Desired Properties

Using the methods described herein, immunoglobulins expressed on the outer surface of a recombinant host cell can be screened for desired binding activity. Immunoglobulins with desired binding activity can be converted to a soluble form and used in assays to identify biological properties of interest. In one embodiment, eukaryotic host cells are transfected with a removable-tether display vector which comprises polynucleotide sequences encoding heavy and light chain variable and constant domains to produce a recombinant eukaryotic host cell.

5.5.1 Host Cells

The removable tether display vectors can be used to transform a eukaryotic or prokaryotic cell for a variety of purposes including, but not limited to, expression of intact immunoglobulins. The mammalian host cells can be derived from any eukaryotic species, including but not limited to mammalian cells (such as rat, mouse, bovine, porcine, sheep, goat, and human), avian cells, fish cells, amphibian cells, reptilian cells, plant cells, and yeast cells. The cells can be maintained according to standard methods well known to those of skill in the art (see, e.g., Freshney (1994) Culture of Animal Cells, A Manual of Basic Technique, (3d ed.) Wiley-Liss, New York; Kuchler et al. (1977) Biochemical Methods in Cell Culture and Virology, Kuchler, R. J., Dowden, Hutchinson and Ross, Inc. and the references cited therein).

Examples of suitable mammalian host cells include HeLa cells (HeLa S3 cells, ATCC CCL2.2), Jurkat cells, Raji cells, Daudi cells, human embryonic kidney cells (293-HEK; ATCC 293c18, ATCC CRL 1573), African green monkey kidney cells (CV-1; Vero; ATCC CRL 1587), SV40-transformed monkey kidney cells (COS-1; ATCC CRL 1650), canine kidney cells (MDCK; ATCC CCL 34), baby hamster kidney cells (BHK-21, BHK-570; ATCC CRL 8544, ATCC CRL 10314), Chinese hamster ovary cells (CHO-K1; ATCC CCL61; CHO DG44 (Chasin et al., 1986, Som Cell Molec Genet, 12, 555)), and other rodent cell lines such as NSO, SP2/O, GH1 (ATCC CCL82), H-4-II-E (ATCC CRL 1548), NIH-3T3 (ATCC CRL 1658).

Other suitable host cells for cloning or expressing the vectors described herein include prokaryotes, yeast or fungal cells. Prokaryotes include gram negative or gram positive organisms, for example *E. coli*, bacilli, pseudomonas species, or *Serratia marcesans*.

Mammalian host cells host cells can be transformed with the removable-tether display vectors using suitable means and cultured in conventional nutrient media modified as is appropriate for inducing promoters, selecting transformants or detecting expression. Representative examples of such methods include transformation using calcium phosphate precipitation (Dubensky et al., 1984, PNAS 81:7529-7533), lipid mediated transfection (e.g., lipofectamine 2000, Invitrogen), direct microinjection of such nucleic acid molecules into intact target cells (Acsadi et al., 1991, Nature 352:815-818), and electroporation (see also US Patent Publication 2004/0115814 for additional methods for introducing vectors into host cells, incorporated herein by reference in its entirety).

Suitable culture conditions for host cells, such as temperature and pH, are well known. In some embodiments, a titration step can be used to dilute the concentration of plasmid used for cellular transfection to reduce the likelihood of expression in the same cell of multiple vectors encoding different immunoglobulins. Freshney (Culture of Animal Cells, a Manual of Basic Technique, third edition Wiley-Liss, New York (1994)) and the references cited therein provide a general guide to the culture of cells). In other embodiments, the titration step can be omitted.

Once transformed, the host cells are incubated under conditions that allow expression of the immunoglobulins. The resulting plasmids can be readily recovered from cells as described (Akamatsu et al., 2007, J Immunol Methods, 327: 40-52).

5.5.2 Screening Methods

Recombinant host cells displaying expressed immunoglobulins can be screened for desired binding activity using affinity-based enrichment assays. In some embodiments, recombinant host cells displaying immunoglobulins are screened for immunoglobulins that bind specifically to a target antigen of interest. Examples of assays suitable for use in the methods described herein include, but are not limited to fluorescence-activated cell sorting (FACS), bead-based sorting such as magnetic bead-based sorting (MACS), or other solid phase panning techniques. Other FACS techniques that can be used in the methods herein are described in J. Immunol. Meth. 1989, 117: 275, are known in the art (such as B-D's FACS 440, Dako-Cytomation's MoFlo; B-D's FACSaria; or Beckman-Coulter's Altras. Reference is also made to J. Immunol. Meth., 2000, 243:13. Daugherty et al. (J. Immunol. Meth., 2000, 243: 211) review cell display library selection using flow cytometry sorters, techniques that can also be used to screen for immunoglobulins having the desired properties.

In some embodiments, one or more of the above techniques can be combined. For example, solid phase panning can be combined with the use of flow cytometers or vice versa. See, for example, N. N. Gangopadhyay et al. (J. Immunol. Meth., 2004, 292: 73) describing a combination useful for the isolation (using flow cytometry sorting) of rare cells (pre-enriched before FACS using cell panning techniques).

ELISA assays can be used to determine the binding affinity of an isolated immunoglobulin toward a target antigen. ELISA assays can be performed on immunoglobulins or immunoglobulins displayed on the cell membrane. See, also, Harlow & Coulter, Antibodies, A Laboratory Manual (1988), for a description of immunoassay formats and conditions that can be used to determine specific immunoreactivity.

In some embodiments, magnetic bead sorting is used to remove antibodies that non-specifically interact with the target antigen of interest. As described in Example 1, magnetic bead-conjugated antibodies can be added to buffer containing the transfected cells displaying immunoglobulins. Cells with non-specific binding activity can be removed directly or indirectly by applying a magnet to the solution. The magnet isolates the magnetic bead-conjugated antibodies and anything bound to them.

By way of illustration, Example 1 describes the use of magnetic bead sorting and FACS to isolate antibodies capable of binding IL-12. The embodiment described in Example 1 can be readily adapted to the identification of antibodies capable of binding any target antigen by a person skilled in the art.

In some embodiments, surface-bound immunoglobulins having desired binding properties are expressed as secreted immunoglobulins. This embodiment is achieved by isolating the eukaryotic recombinant host cells expressing the immunoglobulins having desired binding properties, extracting expression vectors from these cells, transforming *E. coli* cells with the extracted plasmids, and purifying the plasmids from the *E. coli* transformants to get quantities of expression vector sufficient for in vitro manipulations. Methods of extracting expression vectors, transforming *E. coli* with said vectors, and purifying plasmids from *E. coli* transformants are well known in the art. In some embodiments, the functional and/or biophysical properties of identified immunoglobulins are screened in an in vitro assay. Properties of immunoglobulins that can be identified via various in vitro screening assays include, but are not limited to, stability, solubility, affinity for antigen, ADCC, CDC, agonist or antagonistic properties, induction or inhibition of apoptosis, angiogenesis, proliferation, activation or inhibition of signaling pathways. Multiple properties may be screened simultaneously or individually. Proteins may be purified or unpurified, depending on the requirements of the assay.

Various methods can be used to produce the secreted immunoglobulins identified in the affinity assays applied to the membrane-bound forms of the immunoglobulins as described above. Immunoglobulins can be isolated or purified after conversion to a soluble form. The antibodies can be purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. For general guidance in suitable purification techniques, see Protein Purification: Principles and Practice, 3.sup.rd Ed., Scopes, Springer-Verlag, N.Y., 1994, hereby expressly incorporated by reference.

5.6 Immunoglobulin Display Libraries

The removable-tether display vectors can be used to create libraries of immunoglobulins. The display libraries can be used to screen for therapeutic antibody agents useful for treating autoimmune and cancer by identifying immunoglobulins that exhibit differential binding activity toward one or more target antigens of interest. Target antigens of interest include, but are not limited to, IL-6, IL-12, CD38, CD9, CD10, HLA-DR, CD20, CD2, CD3, CD4, CD13, CD14, CD15, CD23, CD 24, CD25, CD33, CD39, CDw40, CD41, CD45R, CD54, CD56, CD71, R1-3, PCA-1, PCA-2, PC1, 62B1, 8A, 8F6, MM4, CEA, VEGF, EGFR, CA 15-3, CA125, CA19-9, Her2, Bcl2, and integrins.

In some embodiments, the mammalian display libraries can be used to screen for therapeutic antibody agents that bind cellular receptors implicated in disease. For example, antibodies that bind cellular receptors comprising the Tumor Necrosis Factor Super Family and chemokine family can be identified using the compositions and methods described herein.

In some embodiments, the removable-tether display vectors are designed to generate immunoglobulin display libraries wherein a plurality, or library, of antibody domain sequences are cloned into a given site within the display vector. In some embodiments, a polynucleotide sequence encoding one or more amino acid within the variable domain CDR and/or framework regions can be randomly mutagenized to create a population of display vectors that can be used to transfect eukaryotic host cells for subsequent binding assays as used herein. In other embodiments, a polynucleotide sequence encoding one or more amino acids within the constant domain of the heavy or light chain constant domains may be randomly mutagenized to create a population of display vectors that can used to transform eukaryotic host cells.

There are a variety of techniques that may be used to efficiently generate libraries of immunoglobulins, including those described or referenced in Molecular Cloning—A Laboratory Manual, 3.sup.rd Ed. (Maniatis, Cold Spring Harbor Laboratory Press, New York, 2001), Current Protocols in Molecular Biology (John Wiley & Sons), U.S. Pat. No. 6,403, 312, U.S. Ser. No. 09/782,004, U.S. Ser. No. 09/927,790, U.S. Ser. No. 10/218,102, PCT WO 01/40091, and PCT WO 02/25588, each of which is incorporated by reference in its entirety. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. A variety of commercially available kits and methods for gene assembly, mutagenesis, vector subcloning, and the like, are available for generating nucleic acids that encode immunoglobulin amino acid sequences.

In some embodiments, the variable domains are generated from an antibody-producing cell isolated from any animal capable of producing antibodies upon immunization. In this embodiment, the target antigen can be used to immunize animals including but not limited to chicken, rabbit, llama, sheep, turkey, quail, trout, shark, camel, mouse, rat, hamster, non-human primate, or human. In some embodiments, variable domains are generated from naturally occurring antibody-producing cells that recognize the target antigen of interest and that are isolated from the animal. In some embodiments, the variable domains are generated from semi-synthetic V genes as described in Akamatsu et al., 1993, J Immunology, 151:4651-4659. Upon isolation of antibody-producing cells, PCR methods are used to amplify variable domain sequences from the antibody-producing cells (see e.g., Sambrook, J., Fritsch, E. F., and Maniatis, T., Molecular Cloning, A Laboratory Manual 2nd ed. (1989)). The PCR fragments are then cloned into the appropriate sites within the display vector to generate intact immunoglobulin genes.

In some embodiments, the mammalian display vectors disclosed herein can be engineered to generate mammalian display libraries for the purpose of identifying and selecting recombinant host cells that express an antibody having desired binding or functional characteristics.

6. EXAMPLES

Example 1

Construction of Chicken-Human Chimeric Immunoglobulin Display Libraries 6.2 Materials and Methods Monoclonal mouse anti-human IL-12 antibody (clone #24910), polyclonal goat anti-mouse IL-12 antibody, recombinant human IL-12, mouse IL-12, human IL-12 p40 subunit, and human IL-23 were purchased from R&D Systems (Minneapolis, Minn.).

An Epstein-Barr virus (EBV)-derived immunoglobulin display vector, pYA104, containing the oriP and the full-length EBNA-1 gene, was derived from pCEP4 (Invitrogen, Carlsbad, Calif.). The region containing the hygromycin resistance gene and the gene expression cassette of pCEP4 was removed by digestion with SalI and NruI, and the PvuII-BamHI fragment of pPuro (Invitrogen) carrying the puromycin resistance gene was inserted. The HindIII, PinAI and SfiI sites in the pPuro-derived fragment were removed by fill-in reaction with Klenow fragment. The longest 3.4 kb BamHI fragment of pYA104 (FIG. 1B) contains, from left to right in the figure, the transcriptional terminator derived from the human C2 complement gene (Moreira et al., 1995), the CMV promoter, a leader peptide, cloning sites for light chain variable regions, the human lambda constant region, an internal ribosome entry site (IRES), a leader peptide, cloning sites for heavy chain variable regions, the human gamma-1 constant region, a glycosidylphosphatidylinositol linkage signal (GPI anchor) derived from human decay-accelerating factor (Medof et al., 1987), and the polyadenylation site from the human gamma-1 gene. The IRES sequence was derived from pIRES2-EGFP (BD Biosciences Clontech, Palo Alto, Calif.). The coding regions of the leader peptides, VL and VH, were derived from the humanized anti-Tac antibody (Queen et al., 1989).

The coding region of human or mouse single-chain IL-12 (Invivogen, San Diego, Calif.), and the extracellular region of human IL-4 receptor α chain (amino acid 1-207) were fused to the human Cκ region (amino acid 108-214) (Kabat et al., 1991) and subcloned into the mammalian expression vector pDL172 (Hinton et al., 2004). The last amino acid of the human Cκ region was changed from a cysteine to a serine to avoid dimerization of fusion proteins.

To generate a chicken immunoglobulin library, a white leghorn chicken was immunized with recombinant human and mouse IL-12, and cDNA was prepared from splenocytes as previously described (Tsurushita et al., 2004). A number of chicken anti-IL-12 scFv antibodies had previously been isolated from a phage display library constructed from the cDNA used in this study (Tsurushita et al., 2004). Chicken Vλ genes were amplified by PCR using the 5' primer NT1152 (5'-CGT TCA GGC CAG AGC GGC CTG ACT CAG CCG TCC TCG G-3'; SEQ ID NO:23) and the 3' primer NT1153 (5'-CTG AGT GGC CTT GGG GGC CCC TAG GAC GGT CAG GGT TGT C-3'; SEQ ID NO:24). PCR amplified Vλ fragment was digested with asymmetric SfiI sites, and ligated with correspondingly digested pYA104 vector. To enrich VH genes derived from IgY, nested PCR was performed. First, cDNA was amplified using a 3' primer specific to the heavy chain constant region of IgY (YA1157 3'-GCA ACA GGC GGA CAA TGG-5'; SEQ ID NO:25) in combination with a 5' primer specific to the region encoding the leader peptide of the chicken VH1 gene segment (YA1156 5'-ATG AGC CCA CTC GTC TCC-3'; SEQ ID NO:26) for 15 cycles. An aliquot of the 1st PCR product was used as a template for a 2nd PCR step using either YA1196 (5'-CGT TCA TCC GGA ACG TTG GAC GAG TCC GGG-3'; SEQ ID NO:27) or YA1197 (5'-CGT TCA ACC GGT ACG TTG GAC GAG TCC GGG-3'; SEQ ID NO:28), as a 5' primer in combination with the 3' primer NT1151 (5'-CTG AGT TGC GGC CGC GAC GAT GAC TTC GGT CCC GTG-3'; SEQ ID NO:29) to obtain VH fragments. After digestion with BspEI (or PinAI) and NotI, VH fragments were cloned between the NgoMIV (which has the same cohesive end as BspEI and PinAI) and NotI sites in pYA 104.

A human embryonic kidney-derived cell line 293c18 (American Type Culture Collection, Manassas, Va.), which expresses the EBNA-1 gene, was used as the host cell for transfection of pYA104. The 293c18 cells were maintained in DME medium supplemented with 10% fetal bovine serum (FBS; HyClone, Logan, Utah) and 0.25 mg/ml G418 at 37° C. in a 7.5% $CO_2$ incubator. Another human embryonic kidney cell line, 293H, was maintained in DME medium containing 10% FBS. LJM-1, a derivative of the mouse proB cell line Ba/F3 expressing human IL-12 receptor β1 and β2 chains (Presky et al., 1996), was maintained in RPMI1640 medium supplemented with 10% FBS and 15 ng/ml recombinant human IL-12.

Library transfection, was performed by premixing 1 μg of library DNA was with 100 μg of pUC18 plasmid. This is an optional step and can be used to reduce the number of multiple library plasmids in a single host cell. The DNA mixture was diluted into 6 ml of Hybridoma-SFM (Invitrogen). Separately, 250 μl of Lipofectamine 2000 (Invitrogen) was diluted with 6 ml of Hybridoma-SFM, and then combined with diluted DNA mixture. After 20 min incubation at RT, the DNA-Lipofectamine mixture was added to culture media of $2.5 \times 10^7$ 293c18 cells in poly-D-lysine coated T75 flasks. Two days after transfection, 0.8 μg/ml puromycin was added to the growth medium. Under this condition, approximately $2.5 \times 10^5$ independent stable transfectants were obtained.

The single-chain human and mouse IL-12-Cκ fusion proteins (schIL12-Cκ and scmIL12-Cκ, respectively) were expressed transiently in culture supernatants of 293H cells. Human IL-4Rα-Cκ fusion protein (hIL4R-Cκ) was produced from a stable transfectant of a mouse myeloma cell line NS0 (European Collection of Animal Cell Cultures, Salisbury, Wiltshire, UK). The production levels of these fusion proteins were estimated by ELISA, using goat anti-human Cκ antibody (Biosource, Camarillo, Calif.) for coating and horseradish peroxidase (HRP)-conjugated goat anti-human Cκ antibody (Southern Biotech, Birmingham, Ala.) for detection.

To produce the soluble form of antibody in a small scale, 20 μl of miniprep DNA diluted in 60 μl of Hybridoma-SFM was mixed with 2.5 μl Lipofectamine diluted in 60 μl of Hybridoma-SFM. After 20 min incubation at room temperature, the mixture was added to each well of 24-well plates containing $6 \times 10^6$ 293c18 in 1 ml of DME medium containing 10% FBS. After 4-7 days, culture supernatants containing soluble antibodies were collected into 96-well assay blocks and saved for further analysis. The production level of each clone was measured by ELISA. MaxiSorp™ plates were coated with goat anti-human IgG, Fcγ fragment antibody (Jackson ImmunoResearch, West Grove, Pa.). Bound antibodies were detected by HRP-conjugated goat anti-human Cλ antibody (Southern Biotech).

Chicken-human chimeric antibodies positive in binding to IL-12 were expressed transiently in 293c18 cells and purified using a HiTrap™ protein A column (Amersham Biosciences, Uppsala, Sweden). Antibodies were eluted from the column with 20 mM sodium citrate (pH 3.5), neutralized with 1.5 M sodium citrate (pH 6.5), and buffer-exchanged with PBS by dialysis.

Anti-human Cκ magnetic beads and FACS were used to enrich for immunoglobulins with IL-12 binding affinity. Anti-human Cκ magnetic beads were prepared as follows: $1 \times 10^8$ Dynabeads Sterile Epoxy (Dynal Biotech, Oslo, Norway) prewashed with Buffer A (0.1M sodium phosphate buffer) was resuspended in 125 μl of Buffer A. Fifty μg of goat anti-human kappa light chain antibody (Antibodies, Inc.) diluted in 125 μl of Buffer A was added to the washed beads and incubated for 16-20 hr at 4° C. on a rotator. The beads were washed four times using 500 μl of Buffer B (0.1% human serum albumin in PBS, pH 7.4). The Dynabeads coated with anti-human Cκ antibody were resuspended in 250 μl of Buffer B.

To eliminate non-specific binders, $2 \times 10^7$ 293c18 stable transfectants expressing chicken-human chimeric antibodies on the surface were washed twice with FACS buffer (2% FBS in PBS) and then incubated with 6 nM hIL4R-Cκ for 1 hr on ice. After washing twice with FACS buffer, cells were incubated in 1 ml of Buffer B containing $10^8$ of anti-human Cκ magnetic beads for 1 hr at 4° C. on a rotator. Cells bound to beads were captured with magnetic force. Unbound cells were collected and grown in DME medium containing 10% FBS, 0.8 μg/ml puromycin and 0.25 mg/ml G418.

To enrich for chicken-human chimeric immunoglobulins that specifically bind to IL-12, approximately $10^7$ of 298c18 stable transfectants were incubated with schIL-12-Cκ fusion proteins at the desired concentration for 1 hr on ice. After washing with FACS buffer twice, cells were stained with PECy5-labeled anti-human IgG, specific to gamma heavy chains (BD Biosciences, San Diego, Calif.) and PE-labeled F(ab')$_2$ goat anti-human Cκ antibodies (Southern Biotech). Stained cells were sorted on a MoFlo MLS (DakoCytomation, Glostrup, Denmark). Sorted cells were grown in DME medium containing 10% FBS, 0.8 μg/ml puromycin and 0.25 mg/ml G418, and analyzed by FACS staining using a FACS-Calibur flow cytometer with CellQuest software (BD Biosciences).

After the final FACS sort, cells were grown in DME medium containing 10% FBS, 0.8 μg/ml puromycin and 0.25 mg/ml G418. Plasmid DNA was extracted using buffers in the QIAprep Spin Miniprep Kit (Qiagen, Valencia, Calif.). Approximately $10^7$ cells washed with PBS were resuspended in 500 μl of P1 buffer containing RNase A and lysed with 500 μl of P2 buffer. After 5 min of incubation at room temperature, 700 μl of N3 buffer was added. The cell lysate was centrifuged for 10 min and the supernatant was extracted with phenol-chloroform, and then precipitated in ethanol. The recovered DNA was digested with DpnI to eliminate plasmid that did not replicated in 293c18 cells. Subsequently, E. coli TOP10 (Invitrogen) was transformed with DpnI-digested plasmid by electroporation and cultured in 100 ml LB broth with 50 μg/ml carbenicillin overnight. Plasmid DNA was then purified using QIAGEN Plasmid Midi Kit (Qiagen). To convert the plasmid into a form suitable for expressing soluble IgG, 1 μg of purified DNA was digested with ClaI and BstBI and then religated to remove the region encoding the GPI signal domain. After transformation, TOP10 colonies containing the plasmids were cultured in 48-well blocks containing 4 ml of LB broth with 50 μg/ml carbenicillin. DNA from individual clones was isolated using the QIAprep 96 Turbo Miniprep Kit (Qiagen).

To detect specific binding to antigen, MaxiSorp™ plates (Nalge Nunc, Rochester, N.Y.) were coated overnight at 4° C. with anti-human Cκ antibodies (BioSource) at 1 μg/ml, or recombinant human IL-12, mouse IL-12, human IL-23, or human IL-12 p40 subunit (R&D Systems) at 0.1 μg/ml in 0.2 M sodium carbonate-bicarbonate buffer (pH 9.4). Plates were then blocked with SuperBlock Blocking Buffer (Pierce, Rockford. IL) for 30 min and washed with washing buffer (PBS containing 0.1% Tween 20). Samples and standards diluted in 100 μl ELISA buffer (PBS containing 1% BSA and 0.1% Tween 20) were added to wells and incubated for 2 hr at room temperature. After washing, HRP-conjugated anti-human Cλ antibodies (Southern Biotech) diluted 1:1000 in ELISA buffer was added. After 1 hr of incubation, plates were washed and bound antibodies were detected by addition of ABTS (or TMB) substrate (Kirkegaard & Perry Laboratories, Gaithersburg, Md.). The reaction was terminated by addition of 100 μl/well of 2% oxalic acid (or 2N $H_2SO_4$) and the absorbance was measured at 415 nm (or 450 nm) using a VERSAmax microplate reader (Molecular Devices, Sunnyvale, Calif.).

For the neutralization assay, LJM-1, a derivative of mouse proB cell line Ba/F3 which requires IL-12 for growth, was used (Presky et al., 1996). LJM-1 cells were starved of IL-12 by washing with and culturing overnight in RPMI 1640 medium containing 10% FBS. Appropriately diluted culture supernatants containing chicken-human chimeric antibodies or purified test antibodies were preincubated with 0.45 ng/ml human IL-12 (or 1 ng/ml mouse IL-12) at final concentration in 100 μl of RPMI 1640 medium containing 10% FBS in 96-well plates for 10 min at room temperature. Subsequently, 100 μl of starved cells at $10^5$/ml were added into each well and incubated for 48 hr at 37° C. in a $CO_2$ incubator. To quantitatively measure the level of cell proliferation, 20 μl of AlamarBlue (Biosource International, Camarillo, Calif.) was added to each well and incubated overnight at 37° C. in a $CO_2$ incubator. The signal was read spectrofluorometrically (excitation at 544 nM, emission at 590 nM) using a SPECTRAmax GEMINI SX microplate reader (Molecular Devices).

6.3 Results

To demonstrate the utility of the display vector illustrated in FIG. 1B, chicken-human chimeric IgG1 antibodies that bind to human IL-12 were generated and characterized. IL-12 is a disulfide-linked, 70 kDa heterodimeric glycoprotein composed of a p40 subunit and a p35 subunit, which plays an important role in the induction of various autoimmune conditions (Trembleau et al., 1995, Immunol Today, 16, 383-6; Romagnani et al., 1997, Curr Opin Immunol 9, 793-9; and Trinchieri, 1998, Int Rev Immunol, 16, 365-96). IL-12 is produced by macrophages and B-lymphocytes, and has multiple effects on T-cells and NK cells, including stimulation of cytotoxic activity, proliferation, and promotion of Th1 development, as well as IFN-γ and TNF production (Trinchieri, 2003, Nat Rev Immunol, 3, 133-46).

PCR-amplified chicken V genes were cloned into asymmetric SfiI-SfiI sites for VL and NgoMIV-NotI sites for VH in pYA104. A chicken antibody library, comprising approximately $3 \times 10^8$ independent clones was obtained. In this library, the chicken V genes were expressed as chimeric molecules with human Cλ and Cγ1 constant regions (FIG. 1C). To evaluate the quality of the PCR-amplified chicken V genes, ten clones were randomly picked from the unselected library and analyzed by DNA sequencing. All encoded different amino acid sequences, especially around the complementarity determining regions (CDRs) (data not shown).

The library plasmid was stably transfected into $2.5 \times 10^7$ 293c18 cells using Lipofectamine 2000 reagent. The transfection efficiency was approximately 1% and most of the transfectants produced one kind of antibody on the surface (data not shown). Approximately $2.5 \times 10^5$ independent stable transfectants expressing chicken-human chimeric IgG molecules on the surface were obtained.

The 293c18 stable transfectants were subjected to negative selection to eliminate cells expressing immunoglobulins that did not specifically bind IL-12. Approximately $2 \times 10^7$ cells were mixed with 6 nM hIL4R-Cκ, a non-IL-12 antigen in which the extracellular region of human IL-4R α chain is fused to human Cκ, and incubated with magnetic beads conjugated with anti-human Cκ antibodies. The cells bound to hIL4R-Cκ were removed by magnetic force. Cells, before and after the negative selection, were stained with 6 nM schIL12-Cκ (single chain human IL-12 fused to human Cκ) to detect the cell population expressing anti-IL-12 antibodies; and with anti-human Ig gamma chain antibodies to monitor the level of antibody expression on the surface (FIGS. 2B and C). More than 50% of the 293c18 transfectants that bound to IL-12 were removed at this step, suggesting that the majority of the transfectants expressed antibodies that were not specific to IL-12.

The 293c18 stable transfectants that did not bind to hIL4R-Cκ were cultured in the growth media containing puromycin and G418, and a FACS-based enrichment was used to identify immunoglobulins capable of binding IL-12. Approximately $10^7$ cells were bound to 6 nM schIL12-Cκ. After washing, the cells were stained with PE-labeled anti-human Cκ antibodies to detect cells bound to IL-12 and with PECy5-labeled anti-human gamma chain antibodies to monitor the surface expression of antibodies. The cell population that bound strongly to IL-12 was collected using a cell sorter and cultured in the growth media. Typically, a few percent of cells were recovered at this step. The selection process was repeated again using 1 nM schIL12-Cκ. A final selection was done using 3 nM schIL12-Cκ in order not to lose moderate IL-12-binders, as neutralizing antibodies are not necessarily strong binders. After each round of selection and culturing, cells were stained with schIL12-Cκ to monitor the level of enrichment of IL-12 binders. As shown in FIGS. 2D, E and F, the population of 293c18 cells expressing anti-IL-12 antibodies increased after each cycle, from 2.2% after the first cycle to 79% after the third cycle. Little binding was observed to hIL4R-Cκ after enrichment (data not shown).

To enrich for antibody clones that were crossreactive to mouse and human IL-12, another screening experiment was carried out using the same initial 293c18 stable transfectants. After the initial negative selection with hIL4R-Cκ, the cells were sorted for those capable of binding to mouse single chain IL-12 fused to human Cκ (scmIL12-Cκ) at 6 nM for the first cycle and 1 nM for the second cycle of enrichment. Six nM and 3 nM of schIL12-Cκ were used for the third and fourth cycles, respectively. After the fourth round of selection and culturing, 25% and 37% of 293c18 cells showed binding to human and mouse IL-12, respectively (data not shown).

After the last round of selection for antibodies capable of binding IL-12, antibody-expressing plasmids were isolated from $10^7$ 293c18 cells and used to transform E. coli cells as described in the Materials and Methods. The antibody expressing plasmids were isolated from E. coli and digested with DpnI to demethylate adenine residues in GATC sequences that may have been methylated by the E. coli Dam adenine methylase. Since DpnI digests GATC sequences only when adenine is methylated, treatment with DpnI eliminates plasmids that did not replicate in 293c18. Following DpnI digestion, the TOP10 cells were transformed by electroporation. Approximately, $10^3$ independent colonies were obtained and plasmid DNA was isolated from them as a mixture. To convert the antibody expression module into the form producing soluble IgG1, purified plasmid was digested with ClaI and BstBI to remove the region encoding the GPI anchor (FIG. 1B). The digested vectors were ligated and used for transformation of TOP10 cells. The colonies were cultured individually in the 96-well format and plasmid DNA was isolated on a small scale. The isolated DNA was used to transfect 293c18 cells in 24-well plates for the transient expression of chicken-human chimeric IgGλ antibodies. Approximately 1 ml of culture supernatant containing soluble IgG was collected from each clone into 96-well blocks for subsequent characterizations.

Figure 3:
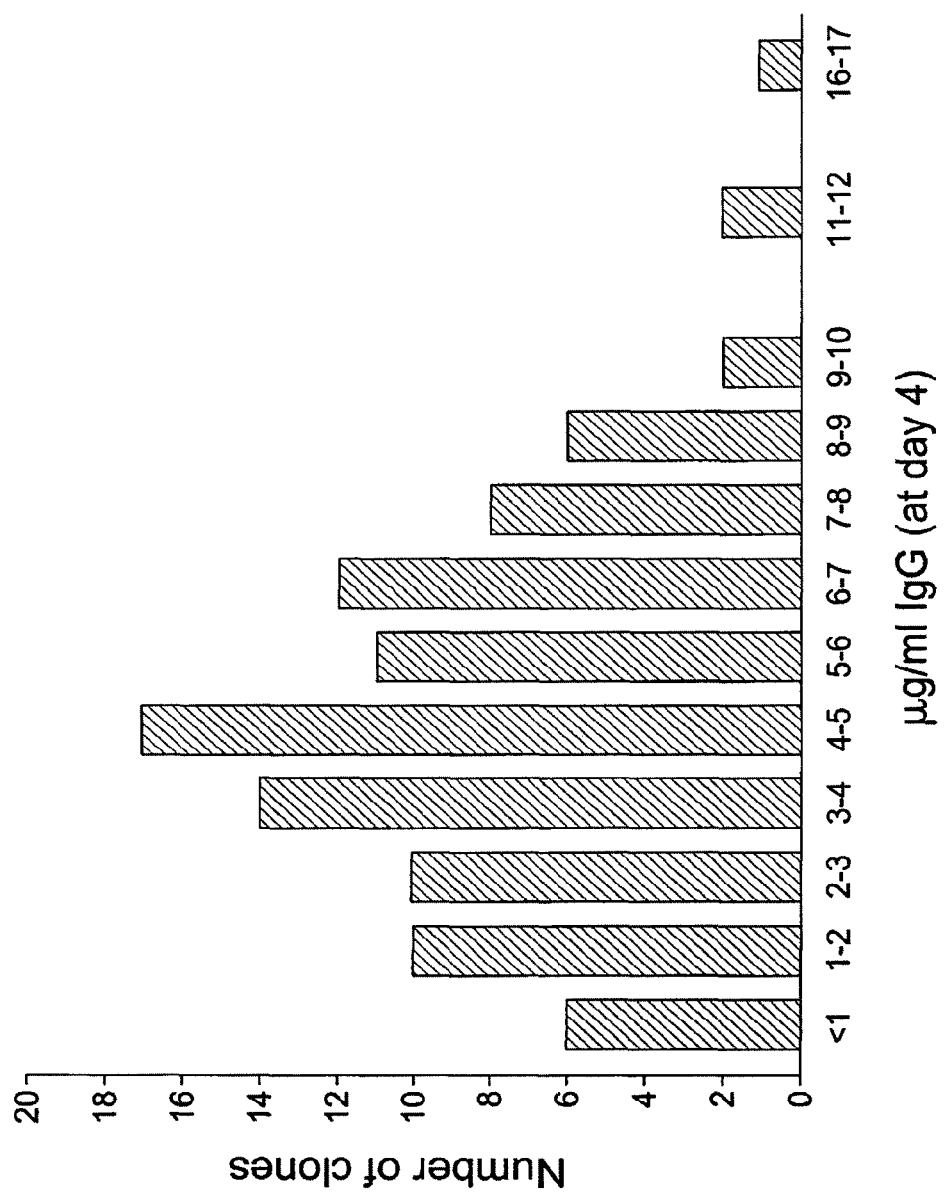
FIG. 3 depicts soluble immunoglobulin levels in transiently expressed culture supernatants from isolated clones.

As described in the Materials and Methods, the production level of antibodies in culture supernatants was measured by ELISA. FIG. 3 shows the distribution of antibody production levels of the 99 clones that were examined, with each clone ranging from 0.11 μg/ml to 16.9 μg/ml, and the average being 4.7±0.3 μg/ml (mean±S.E.) at 4 days after transfection. The vast majority produced more than 1 mg/ml, which should be sufficient for most biological assays. Since the DNA concentrations of the plasmid used in this experiment were within two fold, the variation in the antibody production level (up to 153-fold) is most likely due to the difference in VH and Vλ sequences.

Chicken-human chimeric IgG antibodies in culture supernatants were tested by ELISA for binding to human IL-12, mouse IL-12 and human IL-12 p40 subunit. Binding to hIL4R-Cκ and casein were also tested to evaluate the level of nonspecific binding. As summarized in Table 1, most of the clones obtained in the first and second screenings expressed IgG molecules at the levels shown in FIG. 3. In the first screening, 137 out of 190 (72%) clones were positive in binding to human IL-12. Among them, 78 clones were sequenced and 12 different antibodies were identified. Fifty five percent of human IL-12 binders positively bound to the p40 subunit. Consistent with this result, all the clones that bound to the p40 subunit also bound to human IL-23 (data not shown). Only two clones in the first screening were identified to bind to mouse IL-12. This is probably because the library was enriched only with human IL-12. None of the clones showed binding to hIL4R-Cκ or casein, indicating the robustness of the screening system to eliminate non-specific binders.

TABLE 1

| Selected for: | hIL12[a] | hIL12 + mIL12[b] |
|---|---|---|
| Clones analyzed | 191 | 187 |
| Ig expression[c] | 187/189 (99%) | 187/187 (100%) |
| Binding to hIL-12[c] | 137/190 (72%) | 110/187 (59%) |
| Binding to hp40[c] | 104/190 (55%) | 97/187 (52%) |
| Binding to mIL-12[c] | 2/186 (1%) | 51/187 (27%) |
| Binding to hIL-4R-Cκ | 0/186 (0%) | 1/183 (1%) |
| Binding to casein | 0/186 (0%) | 0/187 (0%) |
| Neutralizing activity[d] | 81/192 (42%) | 91/173 (53%) |

[a]Screened three rounds for human IL-12 at 6 nM, 1 nM and 3 nM;
[b]Screened two rounds for mouse IL-12 at 6 nM and 1 nM, followed by two rounds for human IL-12 at 6 nM and 3 nM;
[c]O.D. > 0.1 at 1/10 dilutions of supernatants are considered as positive in ELISA;
[d]Signals up to 0.8 × maximum signal (0.225 ng/ml hIL-12 alone) at 1/8 dilutions of supernatants are considered as positive in neutralizing activity.

The antibodies isolated in the second screening had a similar number of clones that bound human IL-12, p40 subunit, hIL4R-Cκ and casein. In this screening, 51 out of 187 human IL-12 binders also interacted with mouse IL-12, a consequence of using both human and mouse IL-12 in the enrichment process. These results indicate that the screening procedure enriches for clones with the desired binding specificity.

One of the advantages of the display vector described herein is that soluble IgG molecules are expressed in mammalian cells at the end of the screening procedure. For further characterization of chicken-human chimeric anti-IL-12 antibodies, culture supernatants of transiently transfected 293c18 cells were directly used in the IL-12 neutralization assay with LJM-1 cells. Nearly half of the clones obtained from each of the first and second screenings neutralized human IL-12 (Table 1). After sequencing of the VH and Vλ genes in these clones, three neutralizing antibodies with distinct amino acid sequences were identified. From the first screening, all the neutralizing antibodies, represented by the clone h-B1, had the same VH and Vλ sequences. From the second screening, two clones, represented by mh-C1 and mh-E1, were identified. The VH and Vλ sequences of the three clones aligned with their germline VH and Vλ sequences are shown in FIG. 4. The amino acid sequence of the VH and Vλ sequences appear to be typical for chicken antibodies. The VH sequences of h-B1 and mh-E1 contain a cysteine in each of the CDR2 and CDR3, suggesting disulfide bonding between these two CDR regions.

Figure 5:
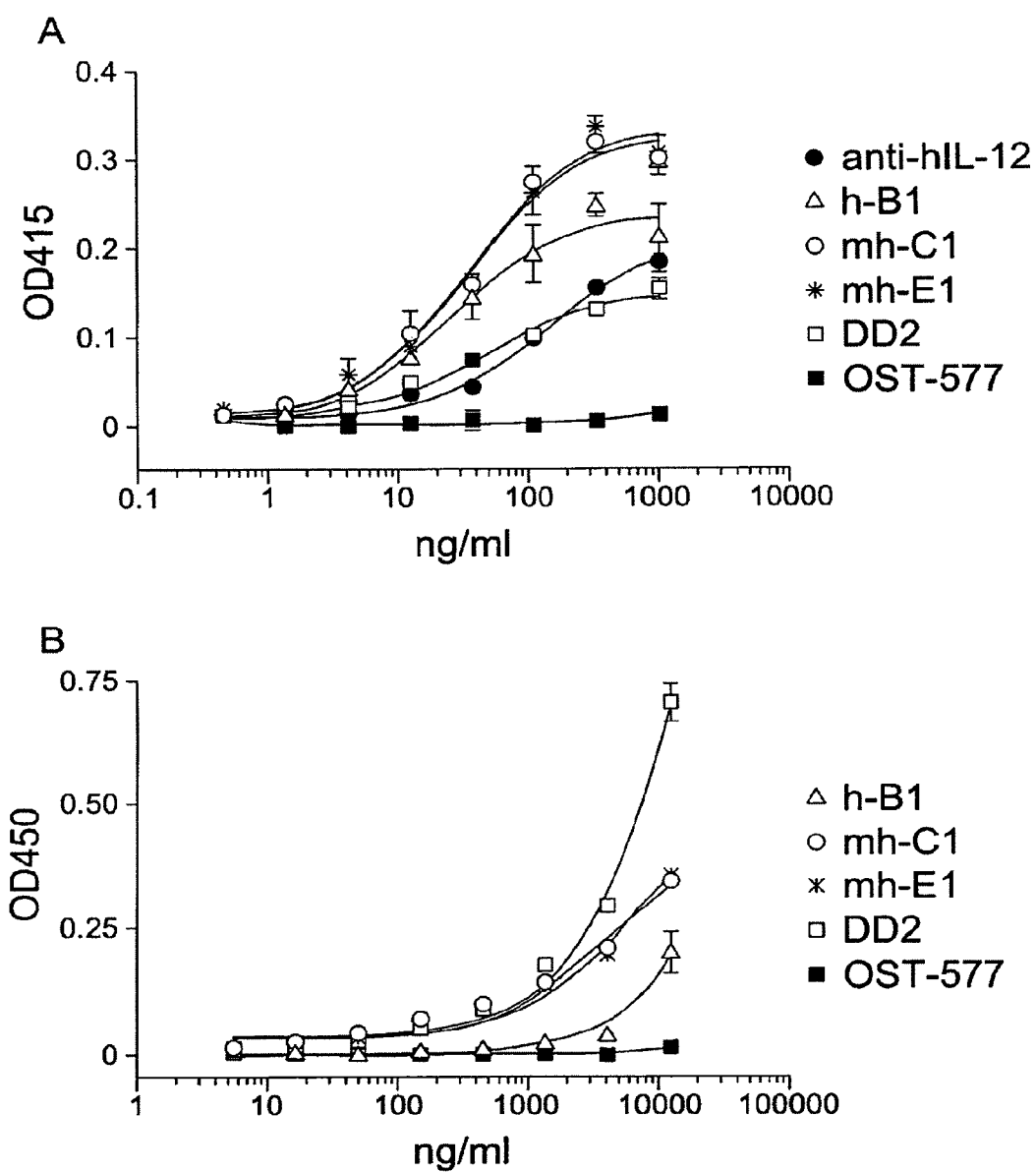
FIGS. 5A-5B depict ELISA binding assays for various immunoglobulins generated using the methods and compositions described herein.

The three chicken-human chimeric IgG antibodies (h-B1, mh-C1 and mh-E1) were purified from culture supernatants of transiently transfected 293c18 cells using a protein A affinity column. The binding of h-B1, mh-C1 and mh-E1 to human IL-12 appeared to be better than that of a commercially available anti-human IL-12 mouse monoclonal antibody (clone #24910, R&D Systems) in ELISA assays (FIG. 5A). The h-B1, mh-C1 and mh-E1 antibodies also weakly bound to mouse IL-12 (FIG. 5B). All three clones bound strongly to the human IL-12 p40 subunit, but not to hIL4R-Cκ or casein (Table 2).

TABLE 2

ELISA reactivity of isolated clones

| Antibodies | Antigen | | | | |
|---|---|---|---|---|---|
| | hIL12 | hp40 | mIL12 | [a]hIL4R-Cκ | casein |
| OST | − | − | − | − | − |
| DD2 | ++ | ++ | ++ | − | − |
| h-B1 | ++ | ++ | + | − | − |
| m-H9 | +++ | +++ | ++ | − | − |
| mh-B1 | ++ | ++ | − | − | − |
| mh-C1 | ++ | ++ | + | − | − |
| mh-E1 | ++ | ++ | + | − | − |
| mh-C8 | + | − | ++ | − | − |
| mh-H6 | − | − | ++ | − | − |
| mh-B9 | ++ | + | ++ | − | − |

+++, very strong reactivity;
++, strong reactivity;
+, weak reactivity;
−, no reactivity;
OST, a human IgG1/λ monoclonal antibody, OST-577 (Ehrlich et al., 1992);
DD2, a chicken/human chimeric anti-IL-12 antibody (Tsurushita et al., 2004);
[a]antigen was captured by pre-coated anti-human Cκ antibody.
Clones h-B1 and m-H9 were identified by screening for either human IL-12 or mouse IL-12, respectively. All the other clones were identified by screening for both human and mouse IL-12. The last three clones were isolated from the library derived from a different chicken. Since none of the clones isolated from this chicken neutralized hIL-12, further characterization was focused on the clones derived from the first chicken.

Figure 6:
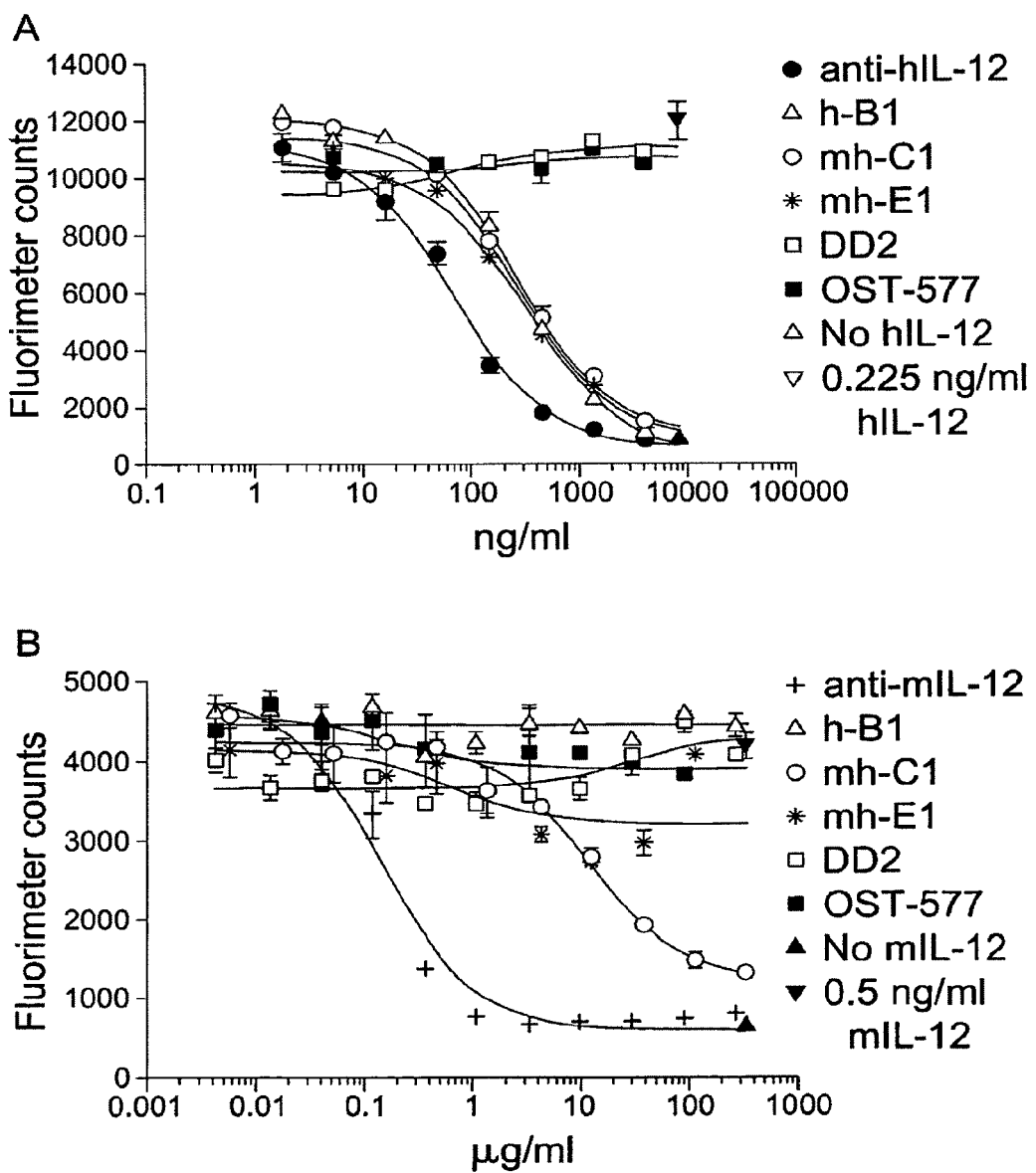
FIGS. 6A-6B depict neutralization assays for various immunoglobulins generated using the methods and compositions described herein.

In the human IL-12 neutralization assay using LJM-1 cells, the three chicken-human chimeric antibodies (h-B1, mh-C1 and mh-E1) showed a similar level of activity, which was only several-fold weaker than the activity of the control mouse neutralizing anti-human IL-12 monoclonal antibody (FIG. 6A). Since mouse IL-12 binds to and is functional with both the mouse and human IL-12 receptors (Schoenhaut et al., 1992, J Immunol, 148, 3433-40), LJM-1 cells were used to analyze how well the three chicken-human chimeric antibodies neutralized mouse IL-12. While h-B1 and mh-E1 showed no neutralization activity to mouse IL-12, mh-C1 showed moderate activity in neutralizing mouse IL-12 (FIG. 6B).

Note that after completion of the disclosed experiments, it was discovered that the GPI signal domain used in these experiments also contained a myc tag N-terminal to the GPI signal domain. Thus, the polynucleotide encoding the GPI signal sequence in these particular experiments comprised the sequence of SEQ ID NO:7, which encodes the amino acid sequence of SEQ ID NO:8.

Example 2

Expression of Removable-Tether Display Vectors Comprising PDGF-R and B7-1 Transmembrane Domains Additional experiments were done to test the ability of PDGF-R and B7-1 (CD80) transmembrane domains to direct expression of antibodies on the cell surface. A derivative of pYA104 expressing kappa light chain, instead of lambda light chain, was used for the experiment. First, the polynucleotides encoding the GPI signal domain was replaced with polynucleotides encoding the human PDGFR-TM domain (nucleotide sequence SEQ ID NO:3; amino acid sequence SEQ ID NO:4) or the murine B7-TM domain (nucleotide sequence SEQ ID NO:5; amino acid sequence SEQ ID NO:6). As with generation of the polynucleotide encoding the GPI signal sequence, the nucleotides encoding the PDGFR-TM and B7-TM domains were amplified using PCR primers that generated a ClaI site at the 5' end of the TM coding sequence and a BstBI site at the 3' end of the TM coding sequence. Then, the PCR fragments encoding variable domains of selected antibodies (Antibody A1, Antibody B, Antibody C (B7 only), and Antibody A2) were cloned into the V gene cloning sites of the display vector. Each transmembrane fusion construct, as well as a construct encoding the GPI signal peptide fused to express Antibody A2, was used to transfect 293c18 cells.

Transfection was performed by premixing 20 ng of vector DNA with 4 µg of pACYC184 plasmid, used as carrier DNA. The DNA mixture was diluted into 250 of Hybridoma-SFM (Invitrogen, Carlsbad, Calif.). Separately, 10 µl of Lipofectamine 2000 (Invitrogen) was diluted with 250 µl of Hybridoma-SFM, and then combined with diluted DNA mixture. After 20 min incubation at RT, the DNA-Lipofectamine mixture was added to culture media of 293c18 cells, seeded at $1 \times 10^6$ per well of 6-well plate on the day before transfection. Two days after transfection, 0.8 µg/ml puromycin was added to the growth medium and cultured for 2 weeks for selection.

To measure the level of surface bound antibody expressed in each of the transfected cells, approximately $2.5 \times 10^5$ of 298c18 stable transfectants were stained with FITC-labeled anti-human IgG, specific to Fc fragment (Jackson ImmunoResearch, West Grove, Pa.). Stained cells were analyzed using a FACS Cyan flow cytometer with Summit software (Dako Cytomation, Fort Collins, Colo.).

Results of this experiment are shown in FIG. 7. Antibodies A1 and B were expressed as fusions to either the B7 or the PDGFR transmembrane domain. Expression levels on the cell surface were higher for both A1 and B antibodies when fused to the B7 transmembrane domain as compared to the A1 and B antibodies fused to the PDGFR transmembrane domain. Antibody C was expressed as a fusion with the PDGFR transmembrane domain or with the DAF GPI linker. Expression of antibody C was greater as a PDGFR transmembrane domain fusion as compared to expression with the GPI linker. Antibody A2 was expressed as a fusion to either the PDGFR transmembrane domain, B7 transmembrane domain, or with the DAF GPI linker. In the case of the antibody A2 fusions, expression was greatest for the PDGFR TM fusion. Expression of the antibody A2 fused to the B7 TM domain was slightly less than that of the PDGFR TM fusion. The antibody A2 expressed with the GPI linker domain had the lowest level of cell surface expression. Thus, the results show that a variety of removable-tether domains are capable of directing varying levels of immunoglobulin expression on the cell surface.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A vector for expressing an antibody fragment comprising:
   an origin of replication;
   a polynucleotide encoding a immunoglobulin constant domain; and, a polynucleotide encoding a cell surface tether domain selected from the group consisting of platelet derived growth factor receptor (PDGF-R) transmembrane domain (SEQ ID NO:4), B7-1 (CD80) transmembrane domain (SEQ ID NO:6), and glycosidylphosphatidylinositol (GPI) signal domain (SEQ ID NO:2),
   wherein said polynucleotide encoding a cell surface tether domain is flanked by a first and a second restriction endonuclease recognition site.

2. The vector of claim 1, wherein said immunoglobulin constant domain comprises a heavy chain constant domain.

3. The vector of claim 2, wherein said immunoglobulin heavy chain constant domain is selected from the mu constant chain domain, the delta constant chain domain, the gamma constant chain domain, the alpha constant chain domain or the epsilon constant chain domains.

4. The vector of claim 2, wherein said heavy chain constant domain comprises a hinge, a CH2 domain, and a CH3 domain.

5. The vector of claim 2, wherein said heavy chain constant domain comprises a hinge.

6. The vector of claim 1, wherein said immunoglobulin constant domain comprises a light chain constant domain.

7. The vector of claim 6, wherein said light chain domain is selected from the kappa constant chain domain or the lambda light chain domain.

8. The vector of claim 2 further comprising:
   a polynucleotide encoding an immunoglobulin light chain variable domain;
   and a polynucleotide encoding an immunoglobulin heavy chain variable domain.

9. The vector of claim 8, further comprising an internal ribosome entry site.

10. The vector of claim 2 further comprising a polynucleotide encoding a heavy chain variable domain.

11. The vector of claim 8, wherein said immunoglobulin light chain variable domain and said immunoglobulin heavy chain variable domain is generated from chicken, rabbit, llama, sheep, mouse, rat, hamster, non-human primate, or human.

12. The vector of claim 2, further comprising a polylinker sequence.

13. The vector of claim 2, wherein said origin of replication is operative in a eukaryotic cell.

14. The vector of claim 13, wherein the origin of replication is the EBV OriP sequence.

15. The vector of claim 14, further comprising a polynucleotide encoding an Epstein-Barr Nuclear Antigen 1 (EBNA-1) protein.

16. The vector of claim 13, wherein said eukaryotic cell is selected from 293-HEK, HeLa, Jurkat, Raji, Daudi, COS, or CV-1 cells.

17. A vector for expressing an antibody fragment comprising:
    an origin of replication;
    a first polynucleotide encoding an immunoglobulin light chain constant domain, wherein;
    a second polynucleotide encoding an immunoglobulin heavy chain constant domain, wherein said constant domain comprises a CH1 domain and a hinge; and
    a polynucleotide encoding a cell surface tether domain selected from the group consisting of platelet derived growth factor receptor (PDGF-R) transmembrane domain (SEQ ID NO:4), B7-1 (CD80) transmembrane domain (SEQ ID NO:6), and glycosidylphosphatidylinositol (GPI) signal domain (SEQ ID NO:2),
    wherein said polynucleotide encoding a cell surface tether domain is flanked by a first and a second restriction endonuclease recognition site.

18. The vector of claim 17 further comprising:
    a polynucleotide encoding an immunoglobulin light chain variable domain;
    and a polynucleotide encoding an immunoglobulin heavy chain variable domain.

19. The vector of claim 17, further comprising a polylinker sequence.

20. The vector of claim 17, further comprising an internal ribosome entry site.

21. The vector of claim 18, wherein said immunoglobulin light chain variable domain and said immunoglobulin heavy chain variable domain is generated from chicken, rabbit, llama, sheep, mouse, rat, hamster, non-human primate, or human.

22. The vector of claim 17, wherein said immunoglobulin heavy chain constant domain is selected from the delta constant chain domain, the gamma constant chain domain, or the alpha constant chain domain.

23. The vector of claim 17, wherein said immunoglobulin light chain constant domain is selected from the kappa constant domain or the lambda constant domain.

24. The vector of claim 17, wherein said origin of replication is operative in a eukaryotic cell.

25. The vector of claim 24, wherein the origin of replication is the EBV OriP sequence.

26. The vector of claim 25, further comprising a polynucleotide encoding an Epstein-Barr Nuclear Antigen 1 (EBNA-1) protein.

27. The vector of claim 24, wherein said eukaryotic cell is selected from 293-HEK, HeLa, Jurkat, Raji, Daudi, COS, or CV-1 cells.

* * * * *

SEQUENCE LISTING

<160> NUMBER OF SEQ ID NOS: 29

<210> SEQ ID NO 1
<211> LENGTH: 111
<212> TYPE: DNA
<213> ORGANISM: Artificial Sequence
<220> FEATURE:
<223> OTHER INFORMATION: Description of Artificial
      Sequence:glycosidylphosphatidylinositol (GPI)
      linkage signal domain, cell surface tether domain,
      GPI anchor

<400> SEQUENCE: 1
ccaaacaaag gaagtggaac cacttcaggt accacccgtc ttctatctgg gcacacgtgc      60
ttcacgttaa caggtttgct tgggacgcta gtaacaatgg gcttgctgac t             111

<210> SEQ ID NO 2
<211> LENGTH: 37
<212> TYPE: PRT
<213> ORGANISM: Artificial Sequence
<220> FEATURE:
<223> OTHER INFORMATION: Description of Artificial
      Sequence:glycosidylphosphatidylinositol (GPI)
      linkage signal domain, cell surface tether domain,
      GPI anchor

<400> SEQUENCE: 2

Pro Asn Lys Gly Ser Gly Thr Thr Ser Gly Thr Thr Arg Leu Leu Ser
 1               5                  10                  15

Gly His Thr Cys Phe Thr Leu Thr Gly Leu Leu Gly Thr Leu Val Thr
            20                  25                  30

Met Gly Leu Leu Thr
        35

<210> SEQ ID NO 3
<211> LENGTH: 147
<212> TYPE: DNA
<213> ORGANISM: Artificial Sequence
<220> FEATURE:
<223> OTHER INFORMATION: Description of Artificial Sequence:human
      platelet derived growth factor receptor (PDGF-R)
      transmembrane domain, human PDGFR-TM domain

<400> SEQUENCE: 3
gctgtgggcc aggacacgca ggaggtcatc gtggtgccac actccttgcc ctttaaggtg      60
gtggtgatct cagccatcct ggccctggtg gtgctcacca tcatctccct tatcatcctc     120
atcatgcttt ggcagaagaa gccacgt                                         147

<210> SEQ ID NO 4
<211> LENGTH: 49
<212> TYPE: PRT
<213> ORGANISM: Artificial Sequence
<220> FEATURE:
<223> OTHER INFORMATION: Description of Artificial Sequence:human
      platelet derived growth factor receptor (PDGF-R)
      transmembrane domain, human PDGFR-TM domain

<400> SEQUENCE: 4

Ala Val Gly Gln Asp Thr Gln Glu Val Ile Val Val Pro His Ser Leu
 1               5                  10                  15

Pro Phe Lys Val Val Val Ile Ser Ala Ile Leu Ala Leu Val Val Leu
            20                  25                  30

Thr Ile Ile Ser Leu Ile Ile Leu Ile Met Leu Trp Gln Lys Lys Pro 35          40          45
Arg

<210> SEQ ID NO 5
<211> LENGTH: 214
<212> TYPE: DNA
<213> ORGANISM: Artificial Sequence
<220> FEATURE:
<223> OTHER INFORMATION: Description of Artificial Sequence:murine B7-1
      (CD80) protein transmembrane domain, B7-TM domain

<400> SEQUENCE: 5
aagcccccag aagaccctcc tgatagcaag aacacacttg tgctctttgg ggcaggattc      60
ggcgcagtaa taacagtcgt cgtcatcgtt gtcatcatca aatgcttctg taagcacaga     120
agctgtttca agaaaatga ggcaagcaga gaaacaaaca cagccttac cttcgggcct      180 gaagaagcat tagctgaaca gaccgtcttc cttt                                 214

<210> SEQ ID NO 6
<211> LENGTH: 71
<212> TYPE: PRT
<213> ORGANISM: Artificial Sequence
<220> FEATURE:
<223> OTHER INFORMATION: Description of Artificial Sequence:murine B7-1
      (CD80) protein transmembrane domain, B7-TM domain

<400> SEQUENCE: 6

Lys Pro Pro Glu Asp Pro Pro Asp Ser Lys Asn Thr Leu Val Leu Phe
 1               5                   10                  15

Gly Ala Gly Phe Gly Ala Val Ile Thr Val Val Ile Val Val Ile
            20                  25                  30

Ile Lys Cys Phe Cys Lys His Arg Ser Cys Phe Arg Arg Asn Glu Ala
        35                  40                  45

Ser Arg Glu Thr Asn Asn Ser Leu Thr Phe Gly Pro Glu Glu Ala Leu
    50                  55                  60

Ala Glu Gln Thr Val Phe Leu
 65                  70

<210> SEQ ID NO 7
<211> LENGTH: 159
<212> TYPE: DNA
<213> ORGANISM: Artificial Sequence
<220> FEATURE:
<223> OTHER INFORMATION: Description of Artificial Sequence:human
      decay-accelerating factor (DAF)
      glycosidylphosphatidylinositol (GPI) signal domain
      containing N-terminal myc tag

<400> SEQUENCE: 7
gaacagaaac tgattagcga agaagacctg aacggcgcta gatccggacc aaacaaagga     60
agtggaacca cttcaggtac cacccgtctt ctatctgggc acacgtgctt cacgttaaca    120
ggtttgcttg ggacgctagt aacaatgggc ttgctgact                            159

<210> SEQ ID NO 8
<211> LENGTH: 53
<212> TYPE: PRT
<213> ORGANISM: Artificial Sequence
<220> FEATURE:
<223> OTHER INFORMATION: Description of Artificial Sequence:human
      decay-accelerating factor (DAF)
      glycosidylphosphatidylinositol (GPI) signal domain
      containing N-terminal myc tag

<400> SEQUENCE: 8

-continued

```
Glu Gln Lys Leu Ile Ser Glu Glu Asp Leu Asn Gly Ala Arg Ser Gly
 1               5                  10                  15

Pro Asn Lys Gly Ser Gly Thr Thr Ser Gly Thr Thr Arg Leu Leu Ser
            20                  25                  30

Gly His Thr Cys Phe Thr Leu Thr Gly Leu Leu Gly Thr Leu Val Thr
         35                  40                  45

Met Gly Leu Leu Thr
     50

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence:light chain
      variable region flanked by non-symmetrical
      restriction endonuclease sites for SfiI

<400> SEQUENCE: 9

Pro Gly Ser Thr Gly Gln Ser Gly Leu Thr Gln Pro Ser
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:light chain
      variable region flanked by non-symmetrical
      restriction endonuclease sites for SfiI

<400> SEQUENCE: 10

Thr Leu Thr Val Leu Gly Ala Pro Lys Ala Ala Pro Ser
 1               5                  10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence:heavy chain
      variable region flanked by symmetrical
      restriction endonuclease sites for NgoMIV and NotI

<400> SEQUENCE: 11

Ala Gly Val His Ser Ala Gly Thr Leu Asp Glu Ser Gly
 1               5                  10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence:heavy chain
      variable region flanked by symmetrical
      restriction endonuclease sites for NgoMIV and NotI

<400> SEQUENCE: 12

Thr Glu Val Ile Val Ala Ala Ala Ser Thr Lys Gly Pro Ser
 1               5                  10

<210> SEQ ID NO 13
<211> LENGTH: 104
<212> TYPE: PRT
<213> ORGANISM: Gallus gallus
<220> FEATURE:
<223> OTHER INFORMATION: chicken Vlambda light chain germ line sequence
```

(Chicken GL)

<400> SEQUENCE: 13

Ala Leu Thr Gln Pro Ser Ser Val Ser Ala Asn Pro Gly Gly Thr Val
1               5                   10                  15

Lys Ile Thr Cys Ser Gly Asp Ser Ser Tyr Tyr Gly Trp Tyr Gln Gln
                20                  25                  30

Lys Ala Pro Gly Ser Ala Pro Val Thr Val Ile Tyr Asp Asn Thr Asn
            35                  40                  45

Arg Pro Ser Asn Ile Pro Ser Arg Phe Ser Gly Ser Lys Ser Gly Ser
        50                  55                  60

Thr Ala Thr Leu Thr Ile Thr Gly Val Arg Ala Asp Asp Asn Ala Val
65                  70                  75                  80

Tyr Tyr Cys Ala Ser Thr Asp Ser Ser Thr Ala Gly Ile Phe Gly
                85                  90                  95

Ala Gly Thr Thr Leu Thr Val Leu
            100

<210> SEQ ID NO 14
<211> LENGTH: 107
<212> TYPE: PRT
<213> ORGANISM: Gallus gallus
<220> FEATURE:
<223> OTHER INFORMATION: rearranged chicken anti-IL12 mh-C1 Vlambda
      light chain VJ exon

<400> SEQUENCE: 14

Gly Leu Thr Gln Pro Ser Ser Val Ser Ala Asn Pro Gly Gly Thr Val
1               5                   10                  15

Glu Ile Thr Cys Ser Gly Gly Gly Ser Tyr Gly Trp His Gln Gln
                20                  25                  30

Lys Ser Pro Gly Ser Ala Pro Val Thr Leu Ile Tyr Tyr Asn Asp Lys
            35                  40                  45

Arg Pro Ser Asn Ile Pro Ser Arg Phe Ser Gly Ser Lys Ser Gly Ser
        50                  55                  60

Thr Ser Thr Leu Thr Ile Thr Gly Val Gln Ala Glu Asp Glu Ala Val
65                  70                  75                  80

Tyr Phe Cys Gly Ser Tyr Glu Gly Ser Thr Tyr Ala Gly Tyr Val Gly
                85                  90                  95

Val Phe Gly Ala Gly Thr Thr Leu Thr Val Leu
            100                 105

<210> SEQ ID NO 15
<211> LENGTH: 102
<212> TYPE: PRT
<213> ORGANISM: Gallus gallus
<220> FEATURE:
<223> OTHER INFORMATION: rearranged chicken anti-IL12 mh-E1 Vlambda
      light chain VJ exon

<400> SEQUENCE: 15

Gly Leu Thr Gln Pro Ser Ser Val Ser Ala Asn Pro Gly Gly Thr Val
1               5                   10                  15

Lys Ile Thr Cys Ser Gly Gly Gly Ser Tyr Gly Trp Tyr Gln Gln
                20                  25                  30

Lys Ser Pro Gly Ser Ala Pro Val Thr Val Ile Tyr Glu Ser Thr Lys
            35                  40                  45

Arg Pro Ser Asp Ile Pro Ser Arg Phe Ser Gly Ser Ala Ser Gly Ser
        50                  55                  60

```
Thr Ala Thr Leu Thr Ile Thr Gly Val Gln Val Glu Asp Glu Ala Val
65                  70                  75                  80

Tyr Tyr Cys Gly Gly Tyr Asp Ser Ser Ala Gly Ile Phe Gly Ala Gly
                85                  90                  95

Thr Thr Leu Thr Val Leu
            100

<210> SEQ ID NO 16
<211> LENGTH: 104
<212> TYPE: PRT
<213> ORGANISM: Gallus gallus
<220> FEATURE:
<223> OTHER INFORMATION: rearranged chicken anti-IL12 h-B1 Vlambda
      light chain VJ exon

<400> SEQUENCE: 16

Gly Leu Thr Gln Pro Ser Ser Val Ser Ala Asn Pro Gly Gly Thr Val
1               5                   10                  15

Glu Ile Thr Cys Ser Gly Ser Ser Gly Ser Tyr Gly Trp Tyr Gln Gln
                20                  25                  30

Lys Ser Pro Gly Ser Ala Pro Val Thr Val Ile Tyr Gln Asn Asp Lys
            35                  40                  45

Arg Pro Ser Asp Ile Pro Ser Arg Phe Ser Gly Ser Lys Ser Gly Ser
    50                  55                  60

Thr Ala Thr Leu Thr Ile Thr Gly Val Arg Ala Glu Asp Glu Ala Val
65                  70                  75                  80

Tyr Tyr Cys Gly Gly Tyr Asp Arg Ser Asn Ser Ser Gly Leu Phe Gly
                85                  90                  95

Ala Gly Thr Thr Leu Thr Val Leu
            100

<210> SEQ ID NO 17
<211> LENGTH: 122
<212> TYPE: PRT
<213> ORGANISM: Gallus gallus
<220> FEATURE:
<223> OTHER INFORMATION: chicken VH heavy chain germ line sequence
      (Chicken GL)

<400> SEQUENCE: 17

Ala Val Thr Leu Asp Glu Ser Gly Gly Gly Leu Gln Thr Pro Gly Phe
1               5                   10                  15

Arg Ala Leu Ser Leu Val Cys Lys Ala Ser Gly Phe Thr Phe Ser Ser
                20                  25                  30

Tyr Asn Met Gly Trp Val Arg Gln Ala Pro Gly Lys Gly Leu Glu Phe
            35                  40                  45

Val Ala Gly Ile Asp Asn Thr Gly Arg Tyr Thr Gly Tyr Gly Ser Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys Ala Ala Gly Thr Ala Gly Ser Ile Asp Ala Trp Gly His
            100                 105                 110

Gly Tyr Gly Thr Glu Val Ile Val Ser Ser
    115                 120

<210> SEQ ID NO 18
<211> LENGTH: 127
<212> TYPE: PRT
```

<213> ORGANISM: Gallus gallus
<220> FEATURE:
<223> OTHER INFORMATION: rearranged chicken anti-IL12 mh-C1 VH heavy
      chain VDJ exon

<400> SEQUENCE: 18

Ala Gly Thr Leu Asp Glu Ser Gly Gly Gly Leu Gln Thr Pro Gly Gly
 1               5                  10                  15

Ala Leu Ser Leu Val Cys Lys Ala Ser Gly Phe Thr Phe Ser Ser His
                20                  25                  30

Gly Met Gly Trp Met Arg Gln Ala Pro Gly Lys Gly Leu Glu Trp Val
            35                  40                  45

Ala Gly Ile Ser Ser Gly Arg Tyr Thr Asn Tyr Gly Ala Ala Val
        50                  55                  60

Lys Gly Arg Ala Thr Ile Ser Arg Asp Asn Gly Gln Ser Thr Val Arg
 65                  70                  75                  80

Met Gln Leu Asn Asn Leu Arg Ala Glu Asp Thr Ala Thr Tyr Tyr Cys
                85                  90                  95

Thr Arg Asp Ser Cys Asn Tyr Gly Cys Trp Tyr Phe Asp Thr Ala Asp
                100                 105                 110

Arg Ile Asp Ala Trp Gly His Gly Thr Glu Val Ile Val Ala Ala
            115                 120                 125

<210> SEQ ID NO 19
<211> LENGTH: 125
<212> TYPE: PRT
<213> ORGANISM: Gallus gallus
<220> FEATURE:
<223> OTHER INFORMATION: rearranged chicken anti-IL12 mh-E1 VH heavy
      chain VDJ exon

<400> SEQUENCE: 19

Ala Gly Thr Leu Asp Glu Ser Gly Gly Gly Leu Gln Thr Pro Gly Gly
 1               5                  10                  15

Ala Leu Ser Leu Val Cys Lys Ala Ser Gly Phe Ser Phe Arg Ser Tyr
                20                  25                  30

Asp Val Ala Trp Val Arg Gln Ala Pro Gly Lys Gly Leu Glu Trp Val
            35                  40                  45

Ala Gly Ile Gly Ser Thr Gly Arg Cys Ile Gly Tyr Gly Ser Ala Val
        50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Pro Glu Asp Thr Ala Thr Tyr Tyr Cys
                85                  90                  95

Ala Lys Glu Ser Gly Thr Gly Cys Gly Trp Ala Ile Tyr Arg Ile
                100                 105                 110

Asp Ala Trp Gly His Gly Thr Glu Val Ile Val Ala Ala
            115                 120                 125

<210> SEQ ID NO 20
<211> LENGTH: 125
<212> TYPE: PRT
<213> ORGANISM: Gallus gallus
<220> FEATURE:
<223> OTHER INFORMATION: rearranged chicken anti-IL12 h-B1 VH heavy
      chain VDJ exon

<400> SEQUENCE: 20

Ala Gly Thr Leu Asp Glu Ser Gly Gly Gly Leu Gln Thr Pro Gly Gly
 1               5                  10                  15

```
Ala Leu Ser Leu Val Cys Lys Ala Ser Gly Phe Ser Phe Arg Ser Tyr
         20                  25                  30

Asp Val Ala Trp Val Arg Gln Ala Pro Gly Lys Gly Leu Glu Trp Val
         35                  40                  45

Ala Gly Ile Gly Ser Thr Gly Arg Cys Thr Tyr Gly Ser Ala Val
     50                  55                  60

Arg Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                 85                  90                  95

Ala Lys Glu Ser Gly Ser Gly Gly Cys Gly Trp Ala Ile Tyr Arg Ile
            100                 105                 110

Asp Ala Trp Gly His Gly Thr Glu Val Ile Val Ala Ala
        115                 120                 125

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence:human IgG
      signal sequence

<400> SEQUENCE: 21

Met Glu Thr Asp Thr Leu Leu Leu Trp Val Leu Leu Leu Trp Val Pro
1               5                   10                  15

Gly Ser Thr Gly
            20

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence:human growth
      hormone signal sequence

<400> SEQUENCE: 22

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence:PCR
      amplification 5' primer NT1152 for chicken Vlambda
      gene

<400> SEQUENCE: 23
cgttcaggcc agagcggcct gactcagccg tcctcgg                           37

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence:PCR
      amplification 3' primer NT1153 for chicken Vlambda
      gene

<400> SEQUENCE: 24
```

-continued

```
ctgagtggcc ttgggggccc ctaggacggt cagggttgtc                            40

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:nested PCR
      1st amplification 3' primer YA1157 specific to heavy
      chain constant region of IgY

<400> SEQUENCE: 25
ggtaacaggc ggacaacg                                                    18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:nested PCR
      1st amplification 5' primer YA1156 specific to region
      encoding leader pepeptide of chicken VH1 gene
      segment

<400> SEQUENCE: 26
atgagcccac tcgtctcc                                                    18

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:nested PCR
      2nd amplification 5' primer YA1196 for VH fragments

<400> SEQUENCE: 27
cgttcatccg gaacgttgga cgagtccggg                                       30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence:nested PCR
      2nd amplification 5' primer YA1197 for VH fragments

<400> SEQUENCE: 28
cgttcaaccg gtacgttgga cgagtccggg                                       30

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence:nested PCR
      2nd amplification 3' primer NT1151 for VH fragments

<400> SEQUENCE: 29
ctgagttgcg gccgcgacga tgacttcggt cccgtg                                36
```